(12) United States Patent
Mabee et al.

(10) Patent No.: US 11,517,044 B2
(45) Date of Patent: Dec. 6, 2022

(54) VAPORIZER APPARATUS

(71) Applicant: MABEE ENGINEERED SOLUTIONS, INC., Shelby Township, MI (US)

(72) Inventors: Brian D. Mabee, Shelby Township, MI (US); Kathryn Mabee, Shelby Township, MI (US); Austin M. Mabee, Shelby Township, MI (US); Marc Longfellow, Ponce Inlet, FL (US)

(73) Assignee: Mabee Engineered Solutions Inc., Shelby Township, MI (US)

( * ) Notice: Subject to any disclaimer, the term of this patent is extended or adjusted under 35 U.S.C. 154(b) by 532 days.

(21) Appl. No.: 16/683,765

(22) Filed: Nov. 14, 2019

(65) Prior Publication Data

US 2021/0052013 A1   Feb. 25, 2021

Related U.S. Application Data

(63) Continuation-in-part of application No. 16/549,241, filed on Aug. 23, 2019, now Pat. No. 11,369,130.

(51) Int. Cl.
*A24F 13/00* (2006.01)
*A24F 17/00* (2006.01)
(Continued)

(52) U.S. Cl.
CPC .............. *A24F 40/05* (2020.01); *F04B 35/04* (2013.01); *F04B 37/06* (2013.01); *F04B 37/20* (2013.01)

(58) Field of Classification Search
CPC .......... A24F 40/10; A24F 40/48; A24F 40/05; A24F 40/485; A24F 40/51; A24F 7/00;
(Continued)

(56) References Cited

U.S. PATENT DOCUMENTS 3,640,001 A * 2/1972 Ellison ...................... F26B 5/04
                                                      392/416
6,176,930 B1 * 1/2001 Koai .................... C23C 16/4486
                                                      118/726
(Continued)

FOREIGN PATENT DOCUMENTS

WO   WO-2017011419 A1 *  1/2017   .......... A24B 15/167
WO   WO-2018152637 A1 *  8/2018
WO   WO-2021041111 A1 *  3/2021   ............ A24F 40/48

*Primary Examiner* — Abdullah A Riyami
*Assistant Examiner* — Thang H Nguyen
(74) *Attorney, Agent, or Firm* — Carrier Blackman & Associates, P.C.; Joseph P. Carrier; Fulchand P. Shende

(57) ABSTRACT

A vaporizer apparatus includes a pump housing, a main housing containing an evacuation chamber, and an operation unit attached to the main housing. The operation unit selectively seals the evacuation chamber off from communication with an air inlet. One or more pumps in the pump housing is/are operable to generate a vacuum in the evacuation chamber. A mouthpiece is attached to the main housing, and may be selectively placed in communication with the evacuation chamber. When oil is placed in the evacuation chamber and the operation unit is operated, the evacuation chamber is temporarily sealed off from the inlet, creating a vacuum sealed chamber connected with the pump(s). Then, the pump(s) is/are activated to reduce pressure in the evacuation chamber, and the oil is vaporized at an ambient temperature without requiring a heater. When the operation unit is released, the evacuation chamber is emptied via the mouthpiece.

16 Claims, 28 Drawing Sheets

(51) Int. Cl.
  *A24F 25/00*   (2006.01)
  *A24F 40/05*   (2020.01)
  *F04B 37/06*   (2006.01)
  *F04B 35/04*   (2006.01)
  *F04B 37/20*   (2006.01)

(58) Field of Classification Search
  CPC ............... A24B 15/167; A61M 11/042; A61M 2205/8206; F04B 35/04; F04B 37/06; F04B 37/14; F04B 37/20; F04B 45/047
  See application file for complete search history.

(56) References Cited

U.S. PATENT DOCUMENTS

| | | | |
|---|---|---|---|
| 2014/0251330 A1* | 9/2014 | Collins | A61M 15/0021 128/203.14 |
| 2018/0199627 A1* | 7/2018 | Bowen | A24D 3/17 |
| 2020/0289770 A1* | 9/2020 | Hebrank | A61M 15/08 |
| 2020/0330706 A1* | 10/2020 | Greenfield | A61M 15/0065 |
| 2021/0052007 A1* | 2/2021 | Mabee | A24F 40/51 |

* cited by examiner

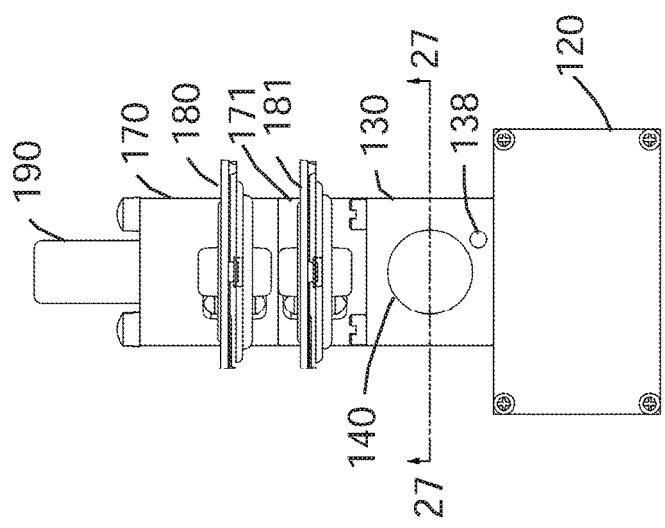
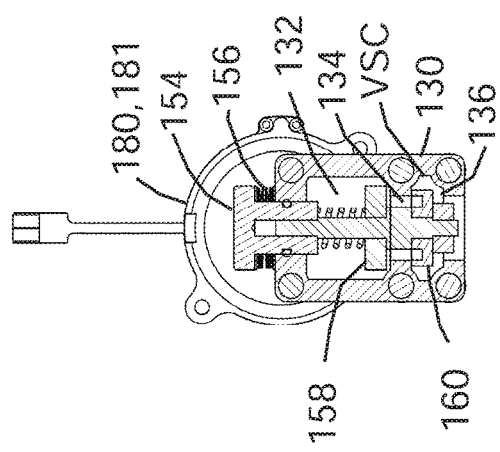
FIG. 26
FIG. 27

VAPORIZER APPARATUS

CROSS-REFERENCE TO RELATED APPLICATIONS

This application is a continuation-in-part of, and claims the benefit of priority from U.S. application Ser. No. 16/549,241, filed on Aug. 23, 2019. The entire disclosure of the referenced priority document, including specification, claims and drawings, is incorporated by reference herein.

BACKGROUND OF THE INVENTION

1. Field of the Invention

The present invention relates to a handheld vaporizer apparatus for vaporizing liquids, such as e-liquids, *cannabis* oil or other vaporizable and inhalable liquids, either at or below ambient room temperature. More particularly, the present invention relates to a handheld vaporizer apparatus that is operable to vaporize oil or other materials at or below ambient room temperature without requiring a heat source or heating element, but rather, by greatly reducing the pressure in a chamber containing the oils or liquids.

2. Description of Related Art

There are several known vaporizers that are configured to vaporize a liquid substance for the purpose of inhaling the vapor. The liquid substance includes e-liquids (commonly referred to as a juice), *cannabis* oil (Cannabidiol (CBD) oil) and Tetrahydrocannabinol ((THC) oil), essential oils, or dry herbs. The known vaporizer apparatus are sometimes referred to as vaporizers, electronic cigarettes, and "vape" or vaping devices.

The liquid substance is stored in a device, such as an atomizer, cartomizer, or clearomizer, which is screwed on to, or otherwise attached to the vaporizer apparatus, and is used to deliver the liquid into vapor form when heated. A typical vaporizer apparatus includes an oil chamber or device for storing oil, a heating element, e.g., a heating coil, a battery which powers the heating coil, and an activation switch or other mechanism for activating the heating coil, which converts the liquid substance to a vapor form, with a mouthpiece that is used by a user to inhale the vapor.

The existing vaporizer apparatus are disadvantageous in requiring the use of a heating element (e.g., a heating coil) for heating, and vaporizing the oil at a temperature that may be loosely controlled or uncontrolled. In some instances, there is a risk of inhaling vapor nearing a combustion temperature, which may injure a person's throat, due to inhalation of a harsh and/or hot vapor.

The temperature of the heating coil used in some vaporizer apparatus may range from 110° C. to 1000° C., depending on wick condition, e.g., dry, wet-through-wick, and full-wet conditions of the vaporizer apparatus. It is also possible that heating the oil may alter the chemical composition of vapor, specifically, if heated at a high temperature.

Vacuum evaporation is a process of causing the pressure in a liquid-filled container to be reduced below the vapor pressure of the liquid, causing the liquid to evaporate at a lower temperature than normal. Vacuum evaporation is a technique that is widely used in some industrial processes such as, for example, wastewater treatment and electroplating. See, for example, the online article on this subject at https://en.wikipedia.org/wiki/vacuum_evaporation.

The present invention has been made to overcome the drawbacks of the existing vaporizer apparatus. Accordingly, it is one of the objects of the present to provide a vaporizer apparatus configured to produce vapor from the oil or liquid at a temperature which is at or below room temperature, without the use of a heat source or heating element.

SUMMARY OF THE INVENTION

The present invention applies the properties of vacuum evaporation to a vaporizing apparatus used to generate an inhalable vapor, in order to avoid a need to include a heater in the apparatus. By creating a temporarily sealed chamber inside of the apparatus which contains a quantity of oil to be vaporized, and by lowering the pressure inside of the chamber, the apparatus is operable to vaporize the oil at ambient temperatures without requiring the use of a heater.

It is believed that by omitting a heater from the vaporizing apparatus, the vaporized oil which is generated by the apparatus will be less toxic, and less hazardous to the health of a user, than the vaporized oil which is generated by conventional "vaping" apparatus which uses a heater.

The present invention, according to one aspect thereof, provides a vaporizer apparatus that can produce vapors from a selected liquid substance at a temperature which is at or below ambient room temperature.

A vaporizer apparatus according to a first embodiment includes a main housing having an evacuation chamber formed therein with an air inlet and an air outlet which communicates with the evacuation chamber.

The vaporizer apparatus according to the first embodiment also includes an operation unit operatively attached to the main housing and configured to be operated by a user, the operation unit configured to selectively and temporarily seal the evacuation chamber off from communication with the air inlet.

The vaporizer apparatus according to the first embodiment also includes a pump operatively connected to the main housing, the pump being in fluid communication with the evacuation chamber, the pump operable to selectively generate a low pressure environment in the evacuation chamber at an ambient temperature.

The vaporizer apparatus according to the first embodiment further includes a mouthpiece attached to the main housing and configured to be selectively placed in fluid communication with the air outlet of the evacuation chamber.

The vaporizer apparatus according to the first embodiment is configured and arranged so that, when an oil is placed in the evacuation chamber and the operation unit is operated, the evacuation chamber is temporarily sealed off from the inlet, thereby creating a vacuum sealed chamber connected with the pump, and the pump is activated to reduce pressure in the evacuation chamber, whereby the oil is vaporized at an ambient temperature without requiring a heater, During operation of the vapor apparatus hereof, when the operation unit is released, the evacuation chamber is placed into fluid communication with the air inlet and also with the mouthpiece.

In one aspect of the vaporizer apparatus according to the first embodiment, the operation unit includes a top seal arranged at a top portion of the evacuation chamber, and a bottom seal disposed in the evacuation chamber below the top seal.

In another aspect of the vaporizer apparatus according to the first embodiment, the operation unit includes a shaft and a magnetic nut mounted at one end portion of the shaft.

In another aspect of the vaporizer apparatus according to the first embodiment, the apparatus further includes a control unit having a microprocessor, and a position sensor in communication with the control unit.

In still another aspect of the vaporizer apparatus according to the first embodiment, the operation unit includes a shaft, a control button mounted on one end portion of the shaft, a top seal arranged at a top portion of the evacuation chamber, a shaft spring mounted on the shaft between the control button and the top seal, and a bottom seal disposed in the evacuation chamber and mounted on the shaft below the top seal.

In operation of the vaporizer apparatus according to the first embodiment, when the control button is pressed, the top seal moves downwardly and seals a top of the evacuation chamber, and the bottom seal seals a bottom of the evacuation chamber.

The pump used as a component of the vaporizer apparatus may be a piezoelectric micro pump.

Another aspect of the present invention provides a method of evaporating a liquid to generate a vapor. This method includes a first step of sealing a chamber with a quantity of liquid therein by closing a valve.

The method includes a second step of activating a vacuum pump which communicates with the chamber via an activation passage, and operating the pump to reduce a pressure inside of the chamber until the liquid evaporates at an ambient temperature without requiring the use of a heater.

The method includes a third step of opening the valve to place the chamber into communication with an outlet; and a fourth step of drawing the vapor outwardly from the chamber via the outlet.

For a more complete understanding of the present invention, the reader is referred to the following, non-limiting, detailed description section, which describes a number of exemplary embodiments of the present invention, and should be read in conjunction with the accompanying drawings. Such exemplary embodiments are provided for illustration and better understanding of the present invention, and are not intended to limit the invention. Throughout the following detailed description and in the drawings, like numbers refer to like parts.

BRIEF DESCRIPTION OF THE DRAWINGS

FIG. 26 is a top plan view, and FIG. 27 is a sectional view taken along the line 27-27 in FIG. 26, of the vaporizer apparatus according to the fourth embodiment hereof.

DETAILED DESCRIPTION OF ILLUSTRATIVE EMBODIMENTS

Illustrative embodiments of vaporizer apparatus according to the present invention will be described hereinafter in detail, with reference to the accompanying drawings. Throughout this description, relative terms like "top", "bottom", "back", "front", "left", "right", and the like are used in reference to a vantage point of a user of the vaporizer apparatus, with the mouthpiece facing toward the user and considered to be at the front of the apparatus. It should be understood that these terms are used for purposes of illustration, and are not intended to limit the invention.

The vaporizer apparatus of the present invention may alternatively be referred to as electronic cigarette, vaping device, or vape device.

First Embodiment

Figure 1:
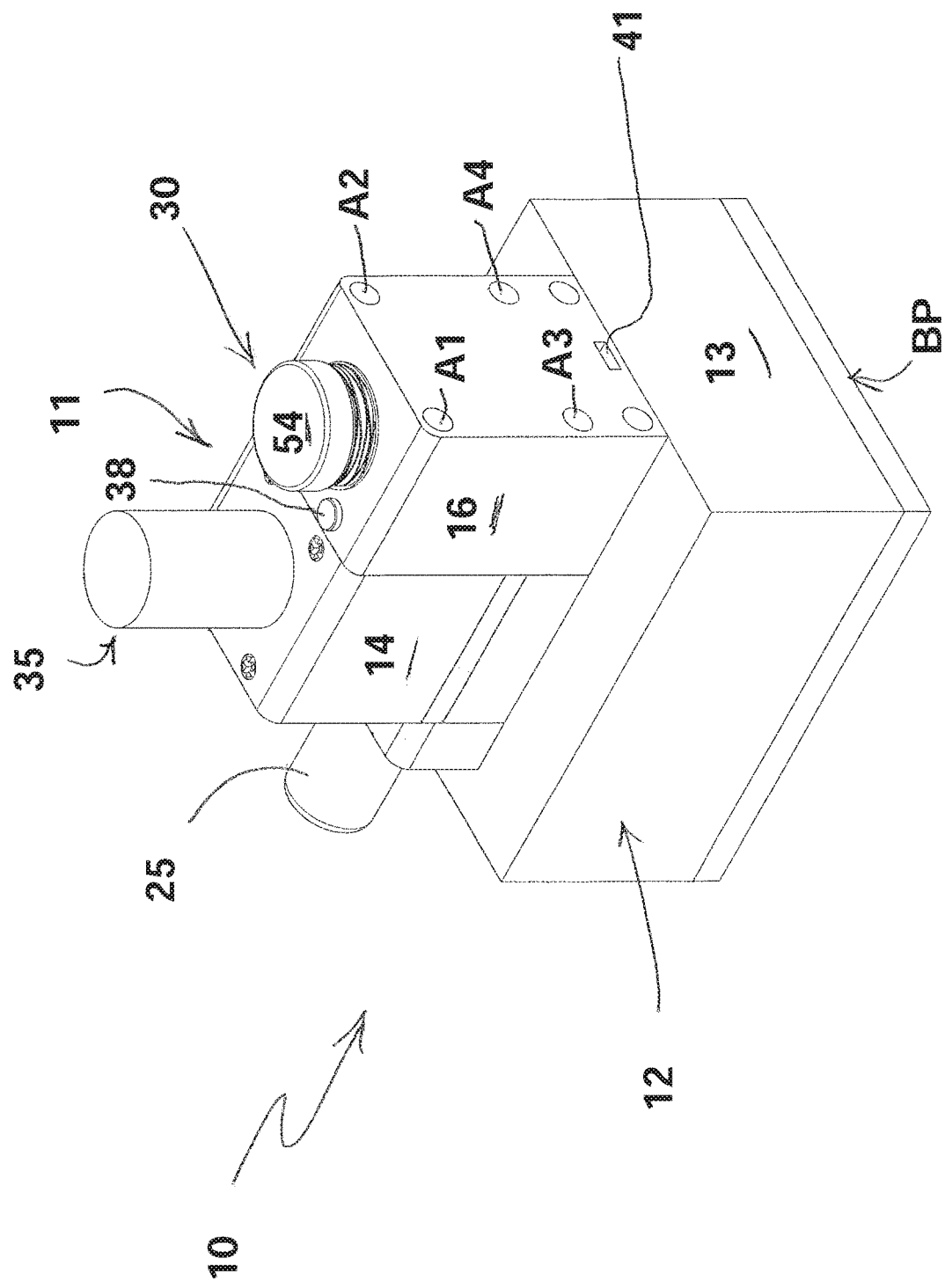
FIG. 1 is a perspective view of a vaporizer apparatus according to a first embodiment of the present invention as viewed from an elevated right rear vantage point.

A vaporizer apparatus 10 according to a first embodiment of the present invention is shown in FIGS. 1-7. FIG. 1 is a perspective view of the vaporizer apparatus 10 according to the first embodiment of the present invention, as viewed from an upper right rear vantage point.

Figure 2A:
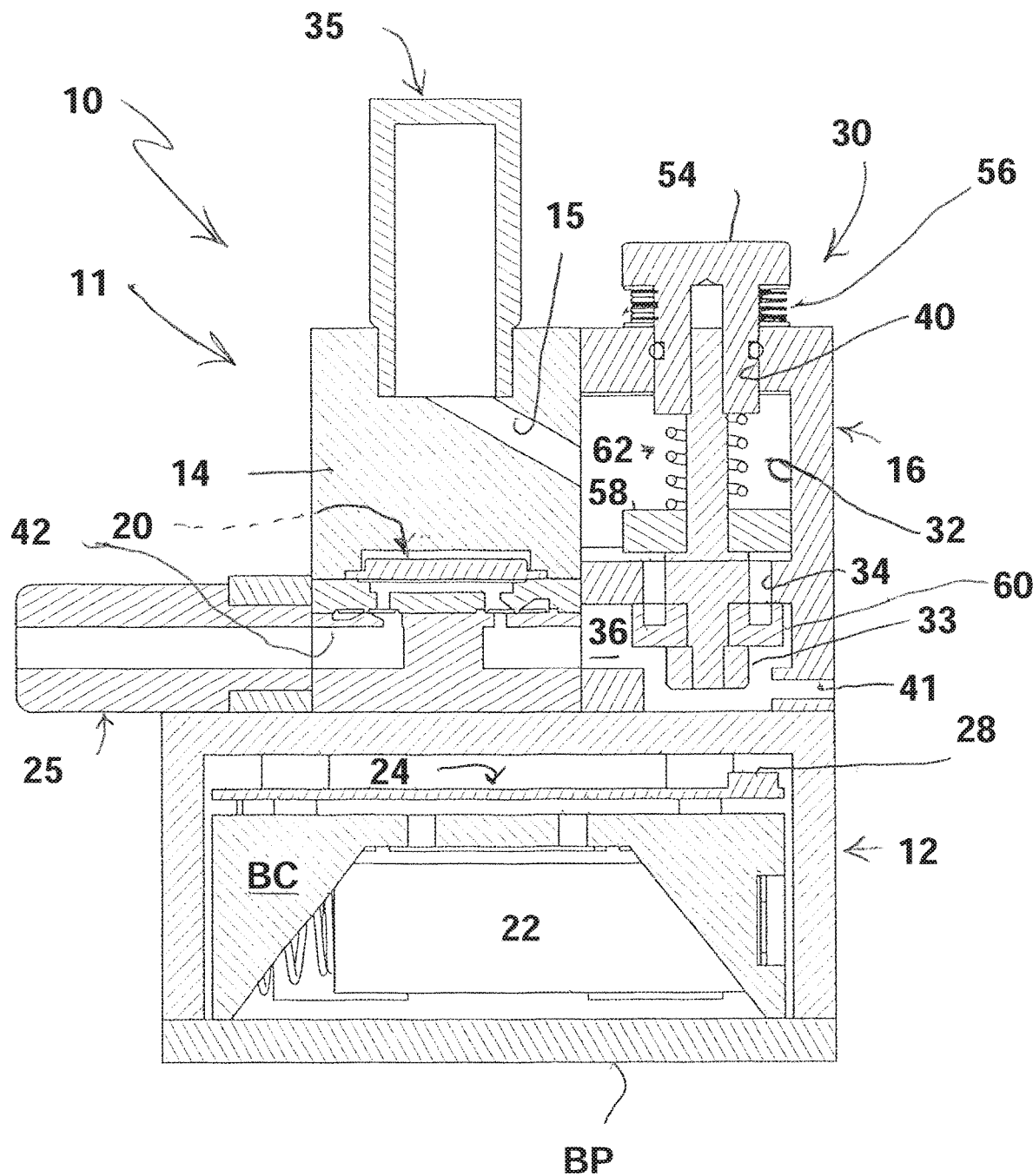
FIG. 2A is a first cross-sectional view of the vaporizer apparatus of FIG. 1, taken along a central longitudinal vertical plane.
Figure 2B:
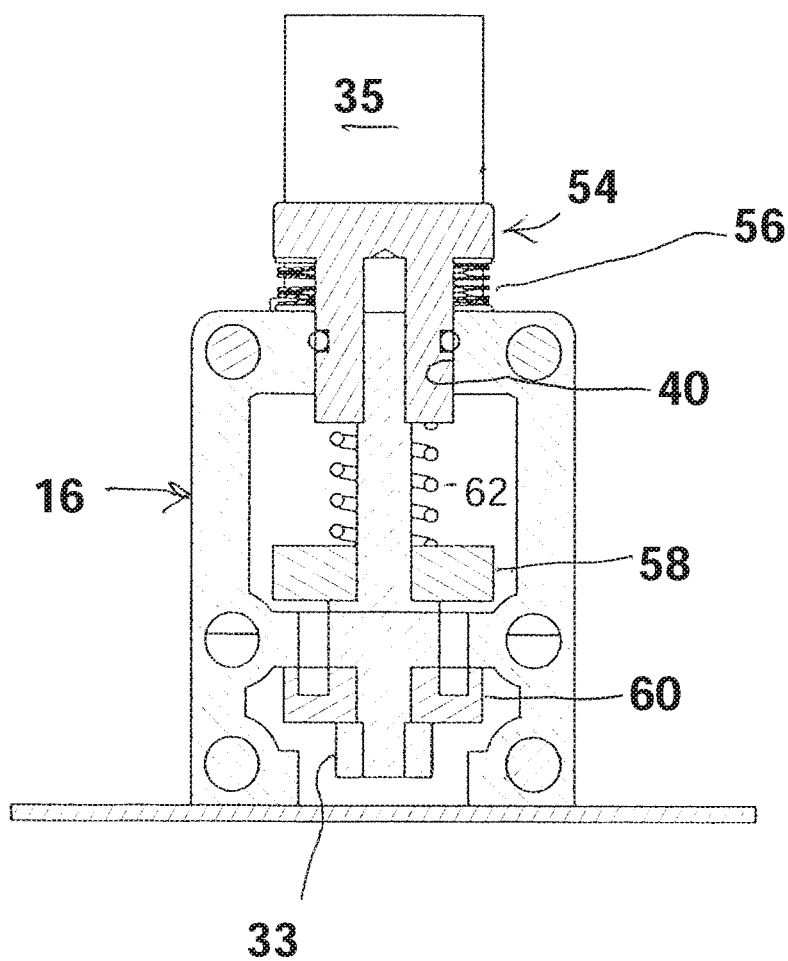
FIG. 2B is a second cross-sectional view of the vaporizer apparatus of FIG. 1, taken along a lateral vertical plane which extends through a central portion of the chamber housing.

FIG. 2A is a first cross-sectional view of the vaporizer apparatus of FIG. 1, taken along a central longitudinal vertical plane. FIG. 2B is a second cross-sectional view of the vaporizer apparatus of FIG. 1, taken along a lateral vertical plane which extends through a central portion of the chamber housing.

Figure 3:
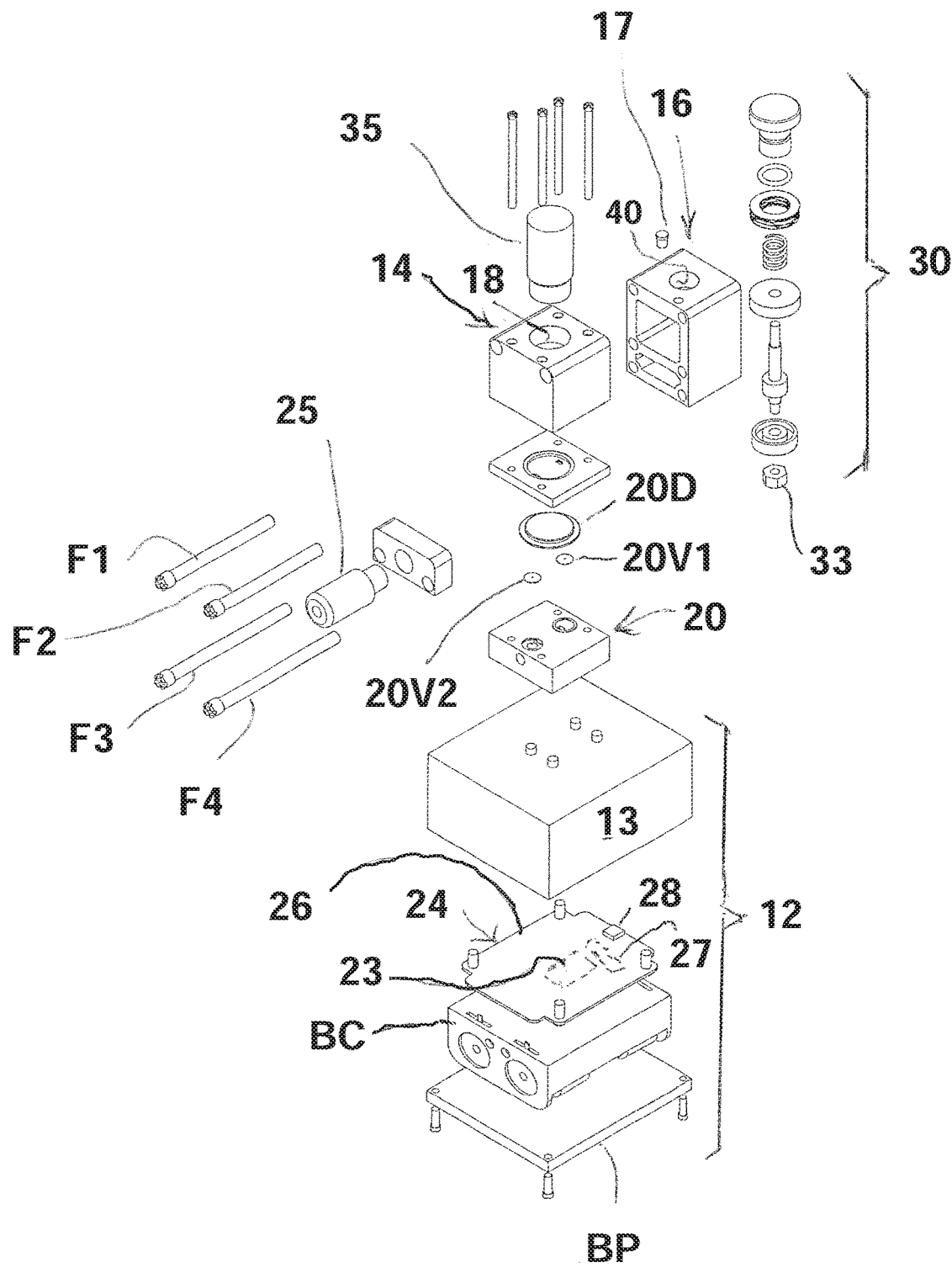
FIG. 3 is an exploded perspective view of the vaporizer apparatus of FIG. 1, as viewed from an upper right front vantage point.

FIG. 3 is an exploded perspective view of the vaporizer apparatus of FIG. 1, as viewed from an upper right front vantage point.

As shown in FIGS. 1-3, the vaporizer apparatus 10 generally includes a main housing 11, a control housing 12 connected to and disposed below the main housing 11, and an operation unit 30 mounted in a hollow bore 40 in the main housing 11. The vaporizer apparatus 10 also includes a pump 20 disposed inside of the main housing 11, and a mouthpiece 25 connected to the main housing 11.

The main housing 11 has two primary components, a pump housing 14, located in the front part thereof adjacent the mouthpiece 25, and a chamber housing 16 disposed behind the pump housing. These may be made as separate components, or alternatively, may be combined into a single unit.

The control housing 12 includes a main case body 13 and a base plate Bp attached to a lower end of the main case body, as will be further described herein.

The pump 20 used in the present invention may be a piezoelectric pump, a micro piezoelectric pump, a piezoelectric diaphragm micropump, or any other type of pump which can be made suitably small. The pump 20 may be entirely concealed inside of the pump housing 14, as shown in the drawings.

As may be seen from FIG. 3, the vaporizer apparatus 10 according to the first embodiment hereof has a modular structure. In other words, the vaporizer apparatus 10 includes several units, i.e., the pump housing 14, the chamber housing 16, the control housing 12, the operation unit 30, and the mouthpiece 25, which are formed as individual units. However, the main housing 11 and the mouthpiece 90 may be integrally formed as a single integral unit structure, or alternatively, the mouthpiece 25 may be integrally formed as part of the pump housing 14.

As shown in FIG. 1, the chamber housing 16 has connecting holes A1, A2, A3, A4 formed therein. The pump housing 14 has corresponding connecting holes B1, B2, B4 and B4 formed therein, which are alignable with the respective connecting holes A1, A2, A3 and A4 of the chamber housing 16. In the depicted embodiment, the chamber housing 16 and the pump housing 14 are connected together using a plurality of fasteners F1, F2, F3 and F4 to arrange the chamber housing 16 and the pump housing 14 in series as shown in FIGS. 1, 2A and 3.

However, as discussed above, in another embodiment the chamber housing 16, the pump housing 14 and the mouthpiece 25 may be formed as one integrated unit.

Control Housing

Further, the main housing 11 and the control housing 12 are connected to one another in similar fashion to that described above.

The control housing 12 may be a box-shaped housing as shown in FIGS. 1-3. However, the control housing 12 may be a cylindrically-shaped housing, a hexagonally-shaped housing, a housing having an oval outline shape, or other suitably-shaped housing.

The control housing 12 includes the main case body 13, which houses a battery case BC therein, as well as a control unit 24 operatively attached to the battery case. The control unit 24 includes a circuit board 26 with a microprocessor 23 and a memory module 27 thereon, as well as a position-sensing device 28 (which may be a Hall effect sensor, an activation switch or other known position-sensing device).

As shown in FIG. 2A, the battery case BC is configured to receive one or more batteries 22 of suitable specification therein. The battery 22 is electrically connected with each of the control unit 24 and the pump 20, and provides power thereto at a desired specification, e.g., at 3V. However, the control unit 24 and the pump 20 may receive power from a different power source in addition to the battery 22 or separate from the battery 22.

The control housing 12 further includes the base plate Bp, as shown. The base plate Bp is held in place on the bottom portion of the main case body 13 using a plurality of fasteners.

The control unit 24 includes a circuit board 26. The position sensor 28 is connected to the circuit board 26, and provides an input signal to the microprocessor 23 on the circuit board 26 when the operation unit 30 is operated (discussed below), and a position of a magnetic nut 33 is changed, due to downward pressure on a control button 54. The position sensor 28 measures the magnitude of a magnetic field of the magnetic nut 33. The position sensor 28 and magnetic nut 33 are used to activate the pump 20 using the control unit 24, but may be substituted with a different activation switch or other suitable mechanism.

The control unit 24 operates the pump 20 based on input received from the position sensor 28, or from an activation switch or other similar mechanism. The control unit 24 may be placed inside of the battery case BC, as shown. Optionally, the control unit 24 may also provide a charging circuit for the batteries 22a as well as modulation circuitry for the pump 20.

The main housing 11 is disposed above the control housing 12 in the depicted embodiment, but other physical arrangements of the components may be used as desired for a particular application.

As may be seen from FIG. 2A, the chamber housing 16 has an oil storage chamber 32, an oil reservoir 34 and an evacuation chamber 36 formed therein. The oil reservoir 34 is formed between the oil chamber 32 and the evacuation chamber 36. In other words, the oil reservoir 34 forms part of an oil path between the oil chamber 32 and the evacuation chamber 36. Further, the chamber housing 16 has a control button opening (also referred to as an operation unit opening) 40 formed therein to receive the operation unit 30.

Optionally, the main housing 11 may have an oil-feeding hole 38 formed therein, and where used, the oil-feeding hole 38 facilitates filling of oil into the interior of the oil chamber 32. The oil feeding hole 38 may be provided in either the pump housing 14 or the chamber housing 16, but in either case, the oil feeding hole is connected to a passage that leads to the oil storage chamber 32.

Optionally, a cap 17 (FIG. 7) may be provided for selectively opening and closing the oil-feeding hole 38. A removable and replaceable oil cartridge 35 may also be temporarily attached to the pump housing 14 by fitting into a bore 18 of the housing, and when so attached, the cartridge 35 may communicate with the oil chamber 32 via an oil inlet passage 15, as shown in FIG. 2A. Alternatively, the cartridge 35 may be made as a "sliding drawer" type unit (not shown) which slidably fits into a corresponding opening in the main housing 11.

Furthermore, the main housing 11 has an air inlet opening 41 and an air outlet opening 42 (FIG. 2A) formed therein.

Operation Unit

The operation unit 30 has a lower portion disposed inside of the chamber housing 16. The operation unit 30 is operable to seal off a top of the oil reservoir 34, and also to seal a bottom of the evacuation chamber 36, thereby trapping oil in the oil reservoir 34 and the evacuation chamber 36, and further, is operable to temporarily create a vacuum sealed chamber VSC (FIG. 8B).

Figure 4:
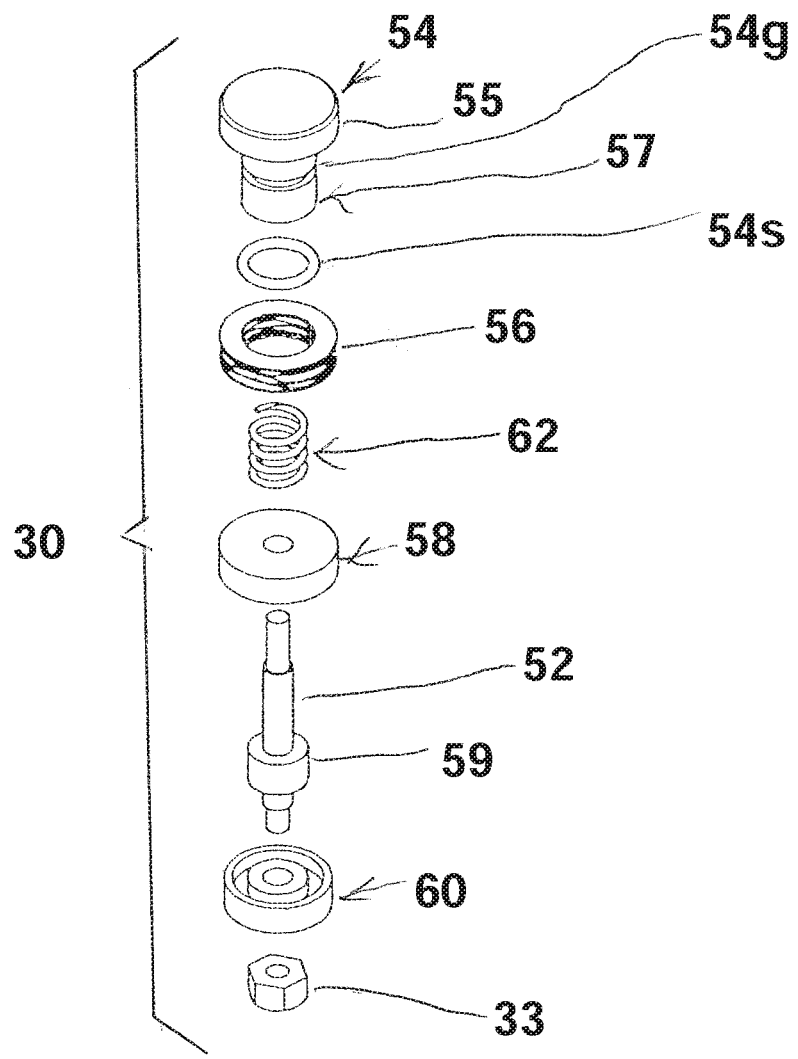
FIG. 4 is a detail exploded perspective view of an operation unit, which is a component subassembly of the vaporizer apparatus according to the first embodiment.
Figure 5:
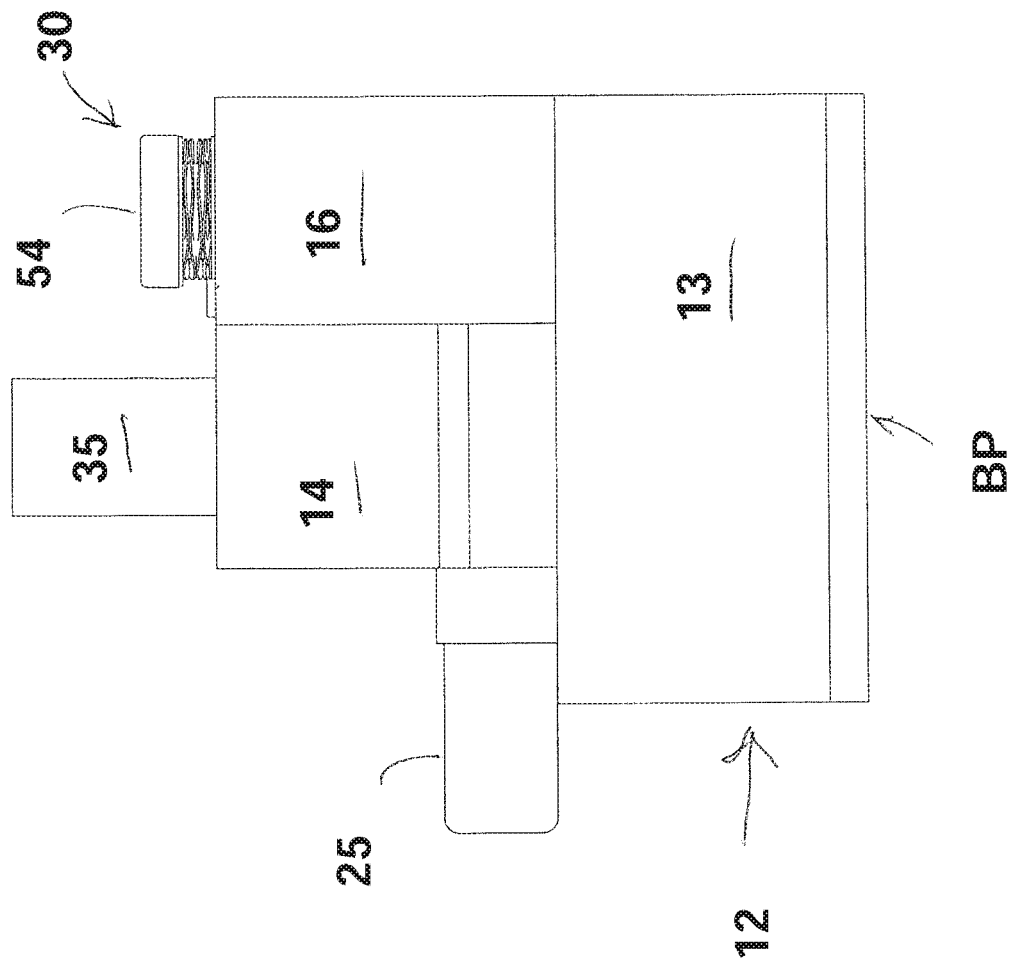
FIG. 5 is a right side plan view of the vaporizer apparatus according to the first embodiment.
Figure 6:
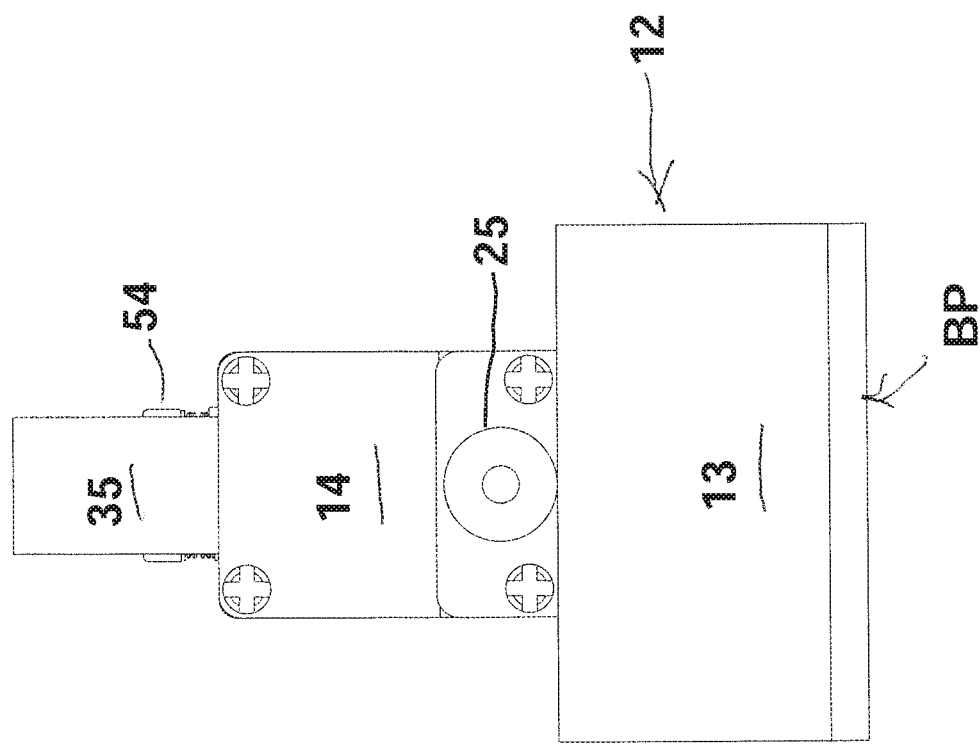
FIG. 6 is a front plan view of the vaporizer apparatus according to the first embodiment.
Figure 7:
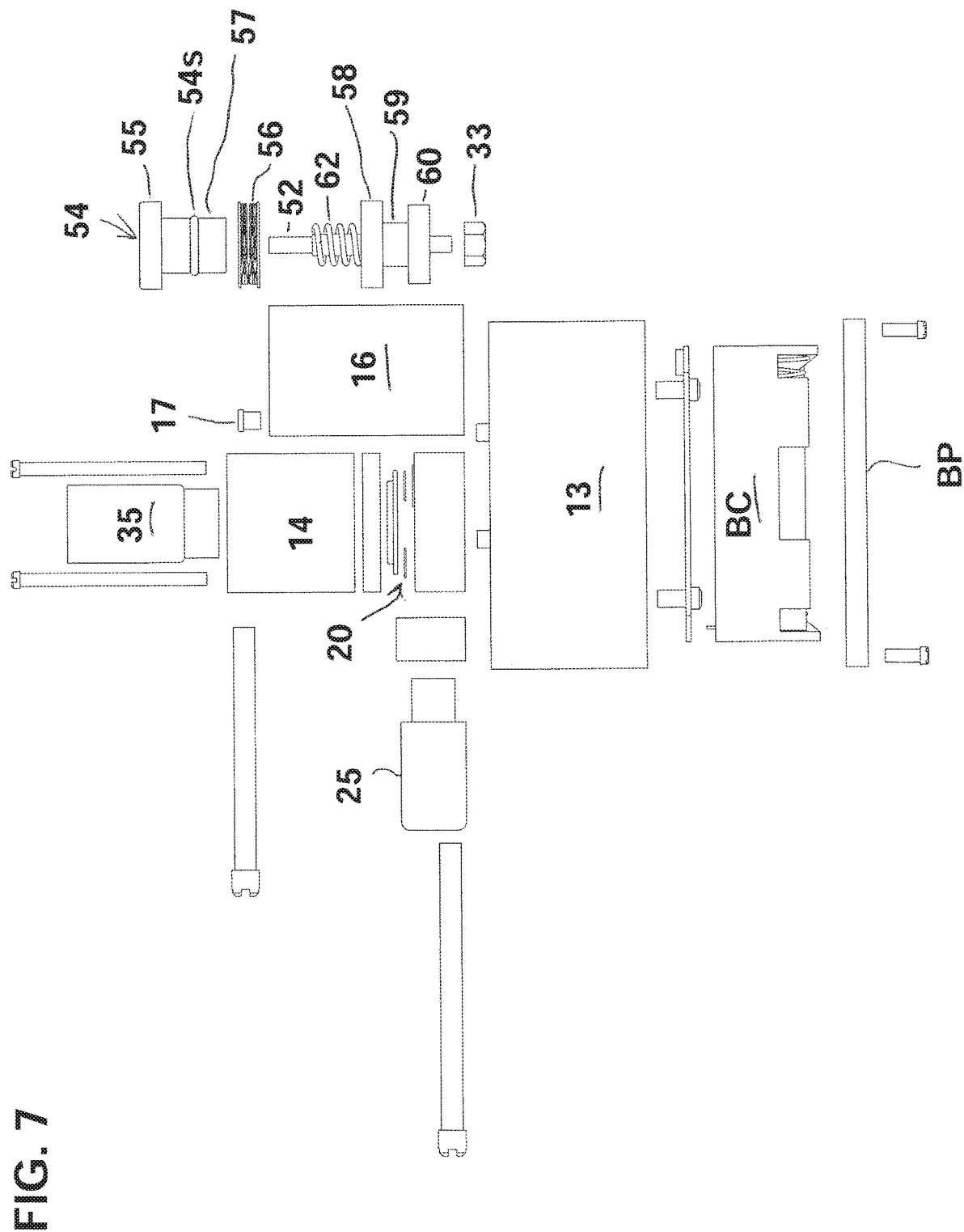
FIG. 7 is an exploded right side plan view of the vaporizer apparatus according to the first embodiment.

Referring now to FIGS. 4 and 7, the operation unit 30 includes a shaft 52 and a control button 54 (also referred to as a top button or an activation mechanism) mounted on the upper end of the shaft 52. The control button 54 has a widened cap portion 55 and a cylindrical body portion 57 disposed below the cap portion. The cylindrical body portion 57 fits slidably into a hollow bore 40 (FIG. 2) formed in the top of the chamber housing 16. Optionally, the cylindrical body portion 57 of the control button 54 may have an annular groove 54g formed therein to receive an O-ring seal 54s.

The operation unit 30 also includes a stacked disc spring (top spring) 56 disposed outside of the chamber housing 16, to provide upward pressure on the control button 54. As seen in FIG. 2B, the disc spring 56 surrounds the body portion 57 of the control button 54, just below the cap portion 55.

The operation unit 30 also includes a shaft spring 62 arranged on the shaft 52, specifically on a portion thereof which is disposed in the oil chamber 32 between the lower end of the control button 54 and a top seal 58. The top seal 58 is arranged proximate to the upper end of the oil reservoir 34, and a bottom seal 60 is disposed on the shaft 52 below an enlarged boss portion 59 thereof, to selectively seal a bottom portion of the evacuation chamber 36. The magnetic nut 33 is attached to a lower end of the shaft 52 below the bottom seal 60.

The stacked disc spring 56, the shaft spring 62, the top seal 58, the bottom seal 60 and the magnetic nut 33 are concentrically arranged along the shaft 52 in a sequence from top to bottom.

As shown in FIGS. 4 and 7, and as noted above, a rubber O-ring seal 54s may be disposed inside of the hollow bore 40 surrounding the lower cylindrical body portion 57 of the control button 54.

Figure 8A:
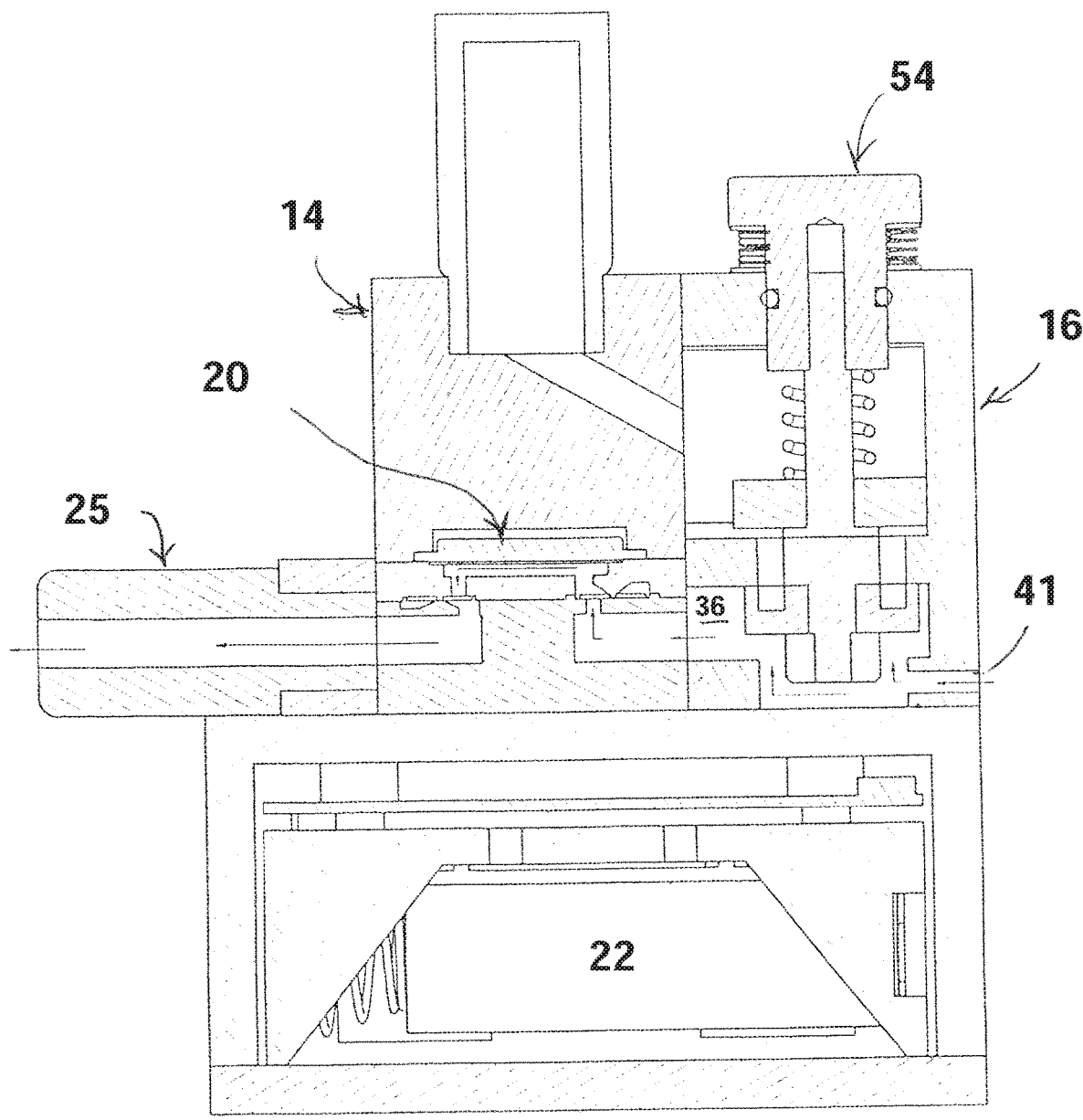
FIG. 8A is a cross-sectional view of the vaporizer apparatus of FIG. 1 similar to FIG. 2A, showing air flow through the apparatus in a configuration where an internal evacuation chamber is open.
Figure 8B:
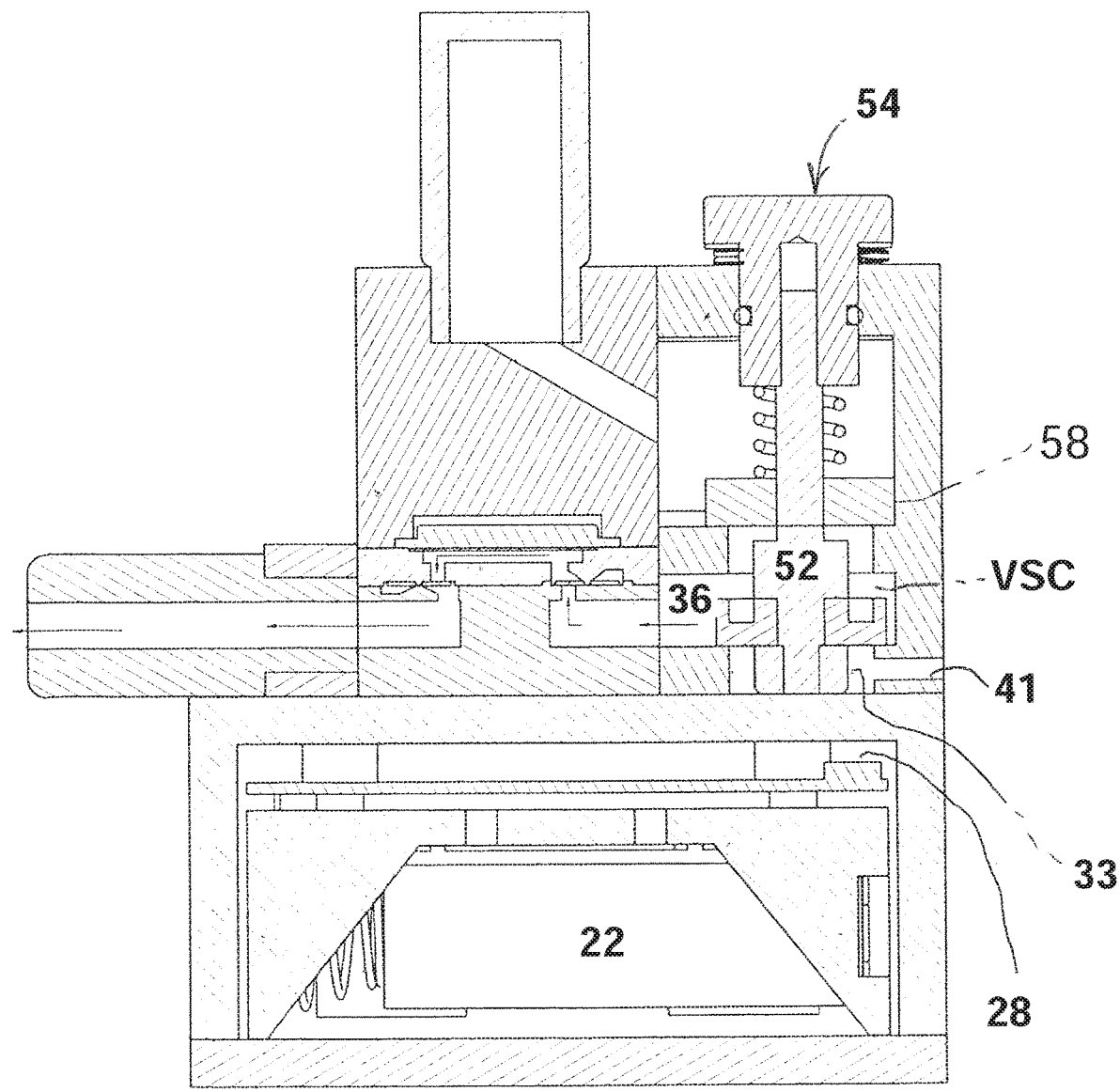
FIG. 8B is a cross-sectional view of the vaporizer apparatus of FIG. 1, similar to FIG. 8A and showing air flow through the apparatus in a configuration where an internal evacuation chamber is closed, and a pump is operating to reduce pressure therein.

FIG. 8A is a longitudinal cross-sectional view of the vaporizing apparatus 10 similar to FIG. 2A, but including arrows showing the flow of air through the apparatus in a first configuration where the control button 54 has not yet been activated, or has been discontinued and raised up after operation. An inlet opening 41 is formed in a lower end of the chamber housing 16, and in this configuration, as shown by the arrows in FIG. 8A, if suction is applied to the mouthpiece 25, air is allowed to flow into the inlet opening, around the magnetic nut 33, through the evacuation chamber 36, and into the pump housing 14, where the air may pass through two sequential one-way valves 20v1, 20v2 (see also FIG. 3) of the pump 20, and the air may then move outwardly into and through the mouthpiece 25.

In contrast to FIG. 8A, FIG. 8B is a longitudinal cross-sectional view of the vaporizing apparatus 10 similar to FIG. 2A, but including arrows showing the flow of air through the apparatus in a second configuration, where the control button 54 has been activated, and the oil chamber 36 has been sealed to form the vacuum sealed chamber VSC. When the control button 54 is pressed downwardly by a user, this pushes the shaft 52 downwardly so that the top seal 58, which is attached to the shaft, forms an airtight seal at the top of the evacuation chamber 36. At the same time, the bottom seal 60 seals off the bottom of the evacuation chamber 36, isolating the evacuation chamber from the inlet 41 to form the vacuum sealed chamber VSC.

At the same time, downward movement of the shaft 52 moves the magnetic nut 33 downwardly, since the nut 33 is attached to the end of the shaft. This makes the proximity sensor 28 send a signal to the microprocessor 23, which turns on power to the pump 20, and the pump operates to lower the pressure (create a vacuum) inside of the evacuation chamber 36. At this time, air is prevented from entering the chamber 36 from the mouthpiece side by the two one-way valves 20v1 and 20v2 of the pump 20.

The control circuit ill initially send 100% power to the pump to vaporize the oil. It will remain at 100% as long as the user holds the control button 54 down. When the reduced pressure inside of the evacuation chamber reaches a specified level, oil which has been placed in the oil chamber 32 will spontaneously be vaporized, due to vapor pressure within the oil. This is accomplished at ambient temperatures, which eliminates any possibility of detrimental effects which could be caused if the oil were to be heated.

When the user releases the control button 54, the vacuum seal/ill be released, and the power to the pump will be reduced to a user-adjustable level and remain on for a user-adjustable time period. This lower power level will be used to clear the vaporized oil out of the evacuation chamber and into the user's mouth. Both the power level and duration of pump operation will be adjustable by the user.

It will be understood that in this embodiment, the operation unit 30 includes a spring-loaded latching mechanism (not shown) which will keep the control button 54 in the down position shown in FIG. 8B after it has been initially pressed a specified distance, and until the control button is pressed downwardly a second time to release the operation unit. These types of spring-loaded latching mechanisms are relatively well known in the art.

Figures 8C, 8D:
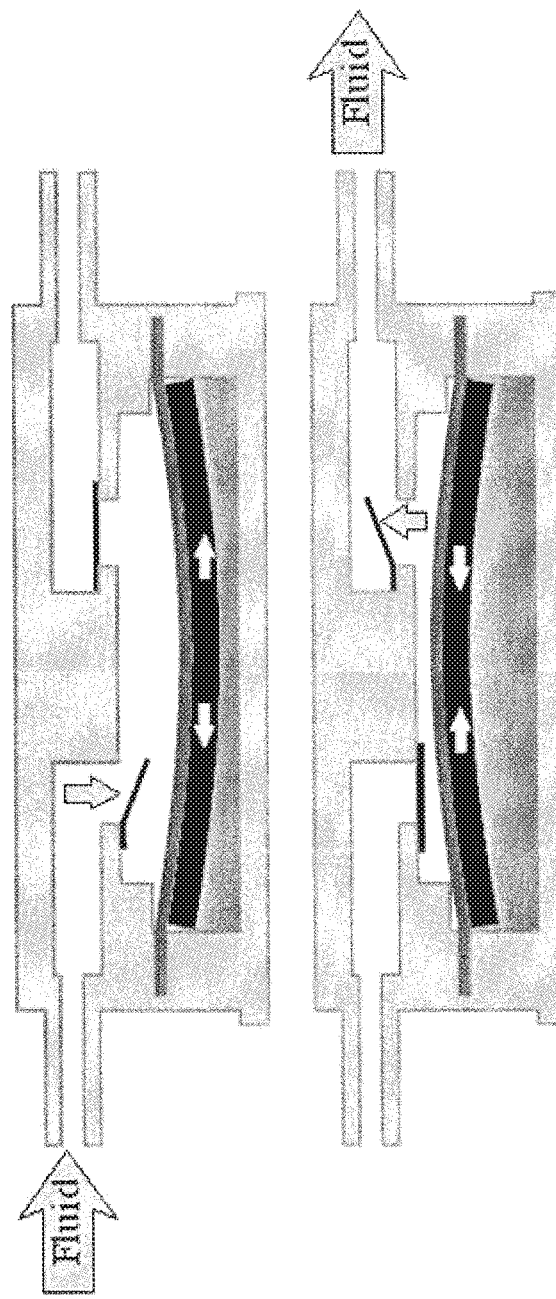
FIGS. 8C and 8D are sequential cross-sectional detail views of a pump which is a component part of the apparatus of FIGS. 1-7.

The pump 20 may be a disc pump, which is a high-performance piezoelectric micropump operating through ultrasonic acoustic resonance. The disc pump can be applied to the pressure-driven flow of liquids. The pump 20 has compact form factor, i.e., it has high portability and it can be tightly integrated into portable devices such as the vaporizer apparatus of the present invention. A pair of cross-sectional detail views showing operation of the pump 20 is shown in FIGS. 8C-8D, in which reciprocating movement of a diaphragm 20D causes air to move through the two one-way valves 20v1, 20v2 of the pump 20 (see also FIG. 3).

Figure 9:
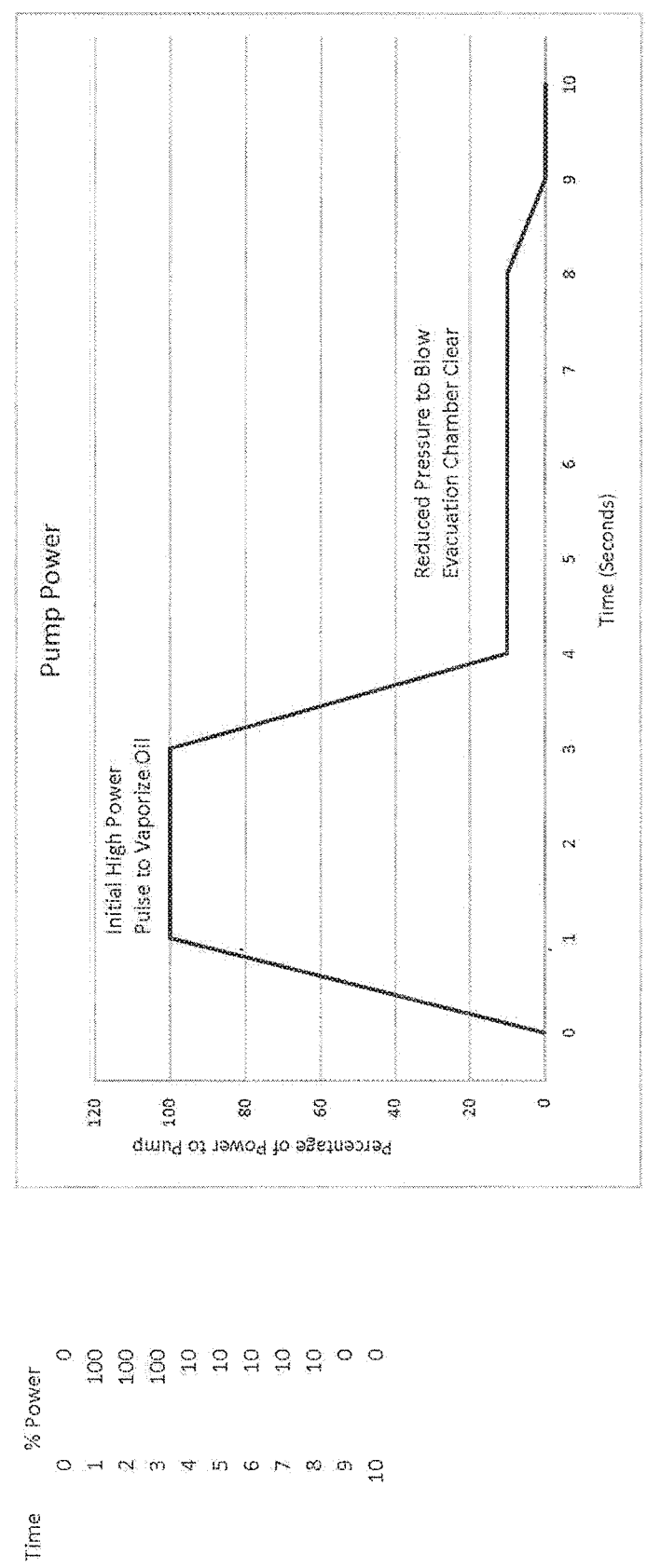
FIG. 9 is a graph showing operation of a pump over time, after a control button is pressed.

FIG. 9 is a graph showing operation of the pump over time after the control button 54 is pressed. At one second after initiation, the pump enters a high power pulse to operate at full speed, in order to vaporize oil in the vacuum sealed chamber VSC. Then, at approximately three seconds after initiation, when the control button 54 is released, power to the pump is reduced to about ten percent, to enable clearing of the evacuation chamber by a user applying suction to the mouthpiece 25. The duration of the reduced power level is adjustable by the user.

The mouthpiece 25 is a cylindrical unit, but may have an oval end portion. The mouthpiece has an inlet opening 92 formed at one end thereof, and an outlet opening 94 formed at the other end thereof. The inlet opening 92 is connected to the outlet opening 78 of the pump housing 14.

The following describes operation of the vaporizer apparatus 10. The present invention works on the principle of gas law, for example, the ideal gas law. The ideal gas law is expressed by the following Equation (1).

$$PV=nRT \quad (1)$$

where,

P is the pressure

V is the volume n is the amount of substance of the gas (in moles)

R is the gas constant (0.08206 L·atm·K−1·mol−1), and

T is the absolute temperature.

According to the present invention, upon operation of the operation unit 30 with reference to FIG. 8B, the top seal 58 isolates the oil reservoir 34 from the oil chamber 32, and the bottom seal 60 seals the bottom of the evacuation chamber 36, so that a vacuum seal is created to temporarily define the vacuum sealed chamber VSC. Further, when the pump 20 is automatically activated upon pressure on the control button 54, which also forms the vacuum seal, operation of the pump 20 causes lowering of pressure for the oil trapped in the oil reservoir 34 and evacuation chamber 36. Soon, the pressure in the vacuum sealed chamber VSC is reduced to a value that causes oil in the oil reservoir 34 and evacuation chamber 36 to vaporize, and the resultant vapor to flow outwardly from the pump toward the mouthpiece 90.

In other words, when the operation unit 30 is operated, i.e., by pressing down the control button (top button) 54 thereof, the shaft 52 is pushed down along with the control button 54, until the top seal 58 (top rubber block) seals off the top of the oil reservoir 34 while trapping oil in the oil reservoir 34. The shaft spring 62 is then further compressed until the bottom seal (bottom rubber block) 60 seals the bottom of the evacuation chamber 36, thereby creating a vacuum seal. Once the vacuum seal is created, the magnetic nut 33 will have reached a point to trigger the position sensor 28, which is operatively connected to the circuit board 26 of the control unit 24 that turns the pump 20 on when the position sensor 28 is triggered. The pump 20 is powered by the battery 22. Upon the turning the pump 20 on, the pressure differential is greatly reduced, causing the oil that was trapped in the oil reservoir 34 and evacuation chamber 36 to vaporize and flow though the pump housing (also referred to as an air flow chamber) and out through the mouthpiece. As previously noted, a pair of sequential sectional views showing operation of a pump is shown in FIGS. 8C-8D.

The oil that was trapped in the oil reservoir 34 and evacuation chamber 36 is not heated or subjected to any heat source for vaporization thereof. Rather, the oil that was trapped in the oil reservoir 34 and evacuation chamber 36 is subjected to a very low pressure, for example, at 1007 mbar or below, for vaporization thereof.

Specifically, when the operation unit 30 is operated, the oil reservoir 34 and the evacuation chamber 36 are isolated from the oil chamber 32, thereby creating a vacuum sealed chamber VSC. Displacement of the shaft 52 also causes further displacement of the magnetic nut 33 that reaches a point of triggering the position sensor 28 that provides signal to the control unit 24 to switch on the pump 20. Operation of the pump 20 reduces the pressure in the vacuum sealed chamber VSC, for example, to a value at or below 1007 mbar, causing vaporization of the oil at or below a room temperature without subjecting the oil to a heat source, e.g., a heating element. As previously noted, the apparatus 10 according to the present invention does not include, or require a heating element. The vapor can be inhaled by the user through the outlet opening of the mouthpiece 25.

In another, modified embodiment, the mouthpiece may act as an activation mechanism for the operation unit. For example, when a user inhales through the mouthpiece, it may trigger the operation unit without the user pressing a control button to turn on the operation unit.

Since the oil is vaporized with no heat source and at or below an ambient room temperature, vapor thus produced is at a low temperature that is not hot. Thus, the vaporizer apparatus 10 of the present invention cannot cause any heat-related injury to a user. Moreover, since the oil is not heated or is not subjected to a heat source of any kind, the alteration of composition of the oil due to heat can be reduced or prevented.

Second Embodiment

Figure 10A:
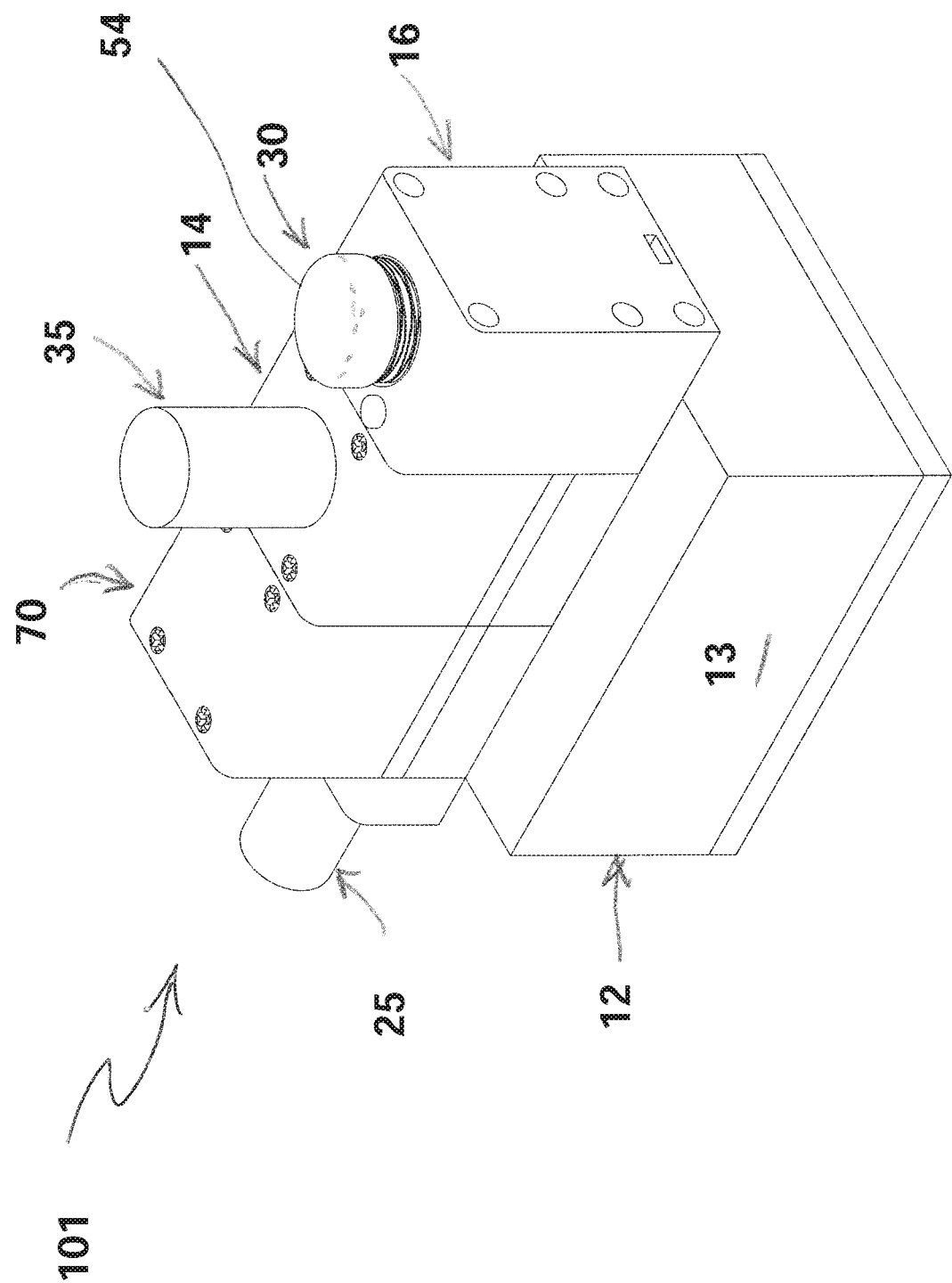
FIG. 10A is a perspective view of a vaporizer apparatus as viewed from a right rear elevated vantage point according to a second embodiment of the present invention.
Figure 10B:
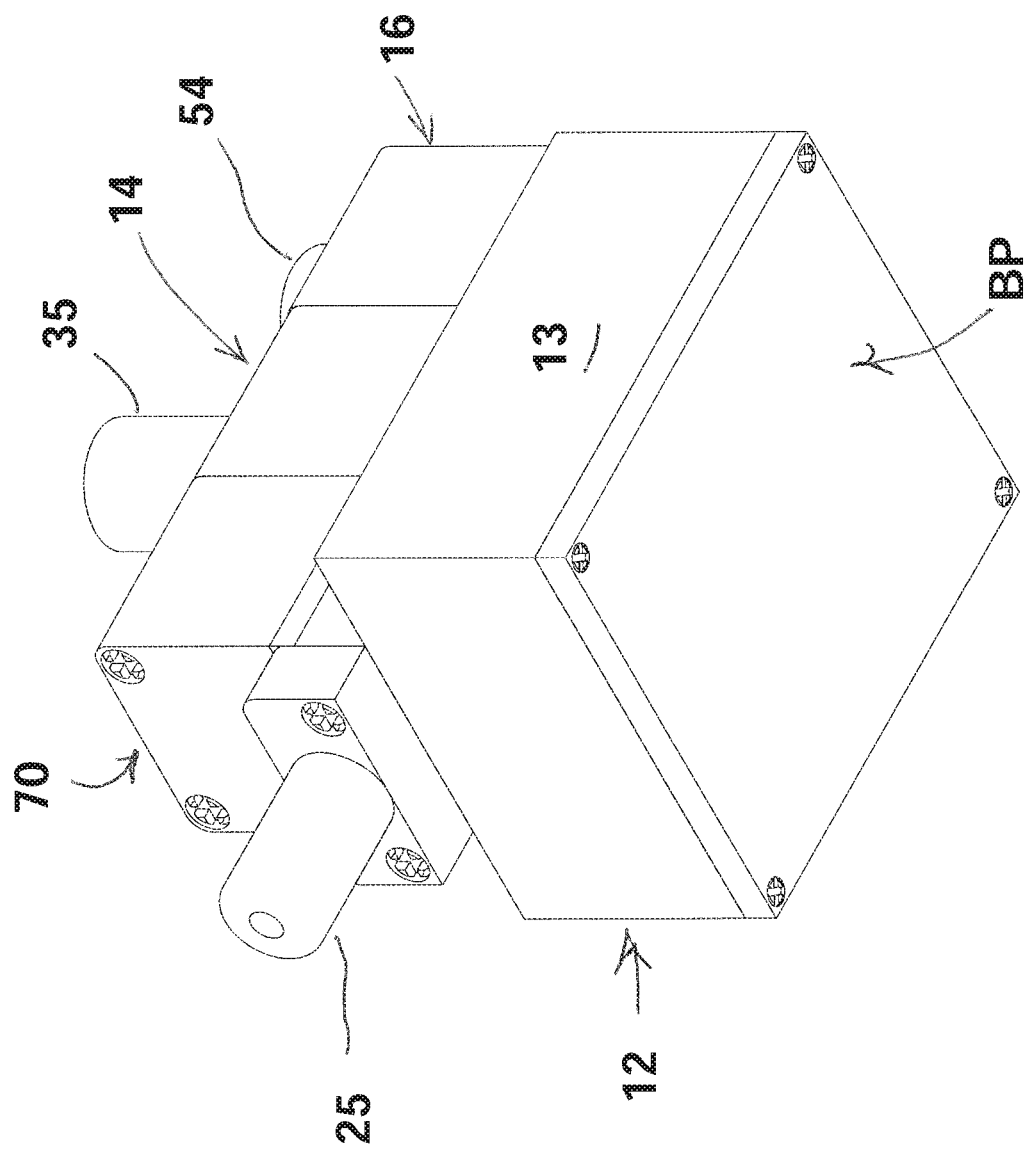
FIG. 10B is a perspective view of the vaporizer apparatus of FIG. 10A as viewed from a lower right vantage point.
Figure 11:
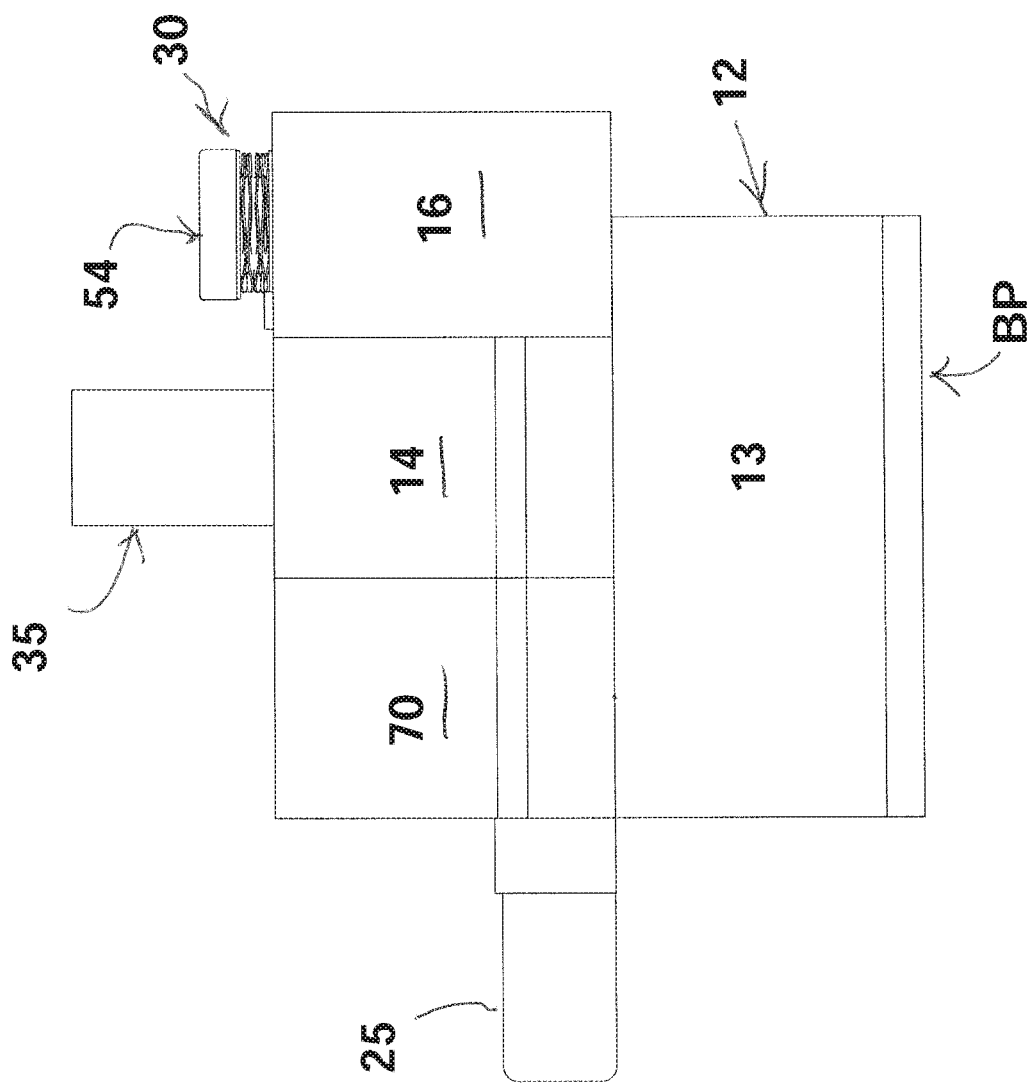
FIG. 11 is a right side plan view of the vaporizer apparatus according to the second embodiment.
Figure 12:
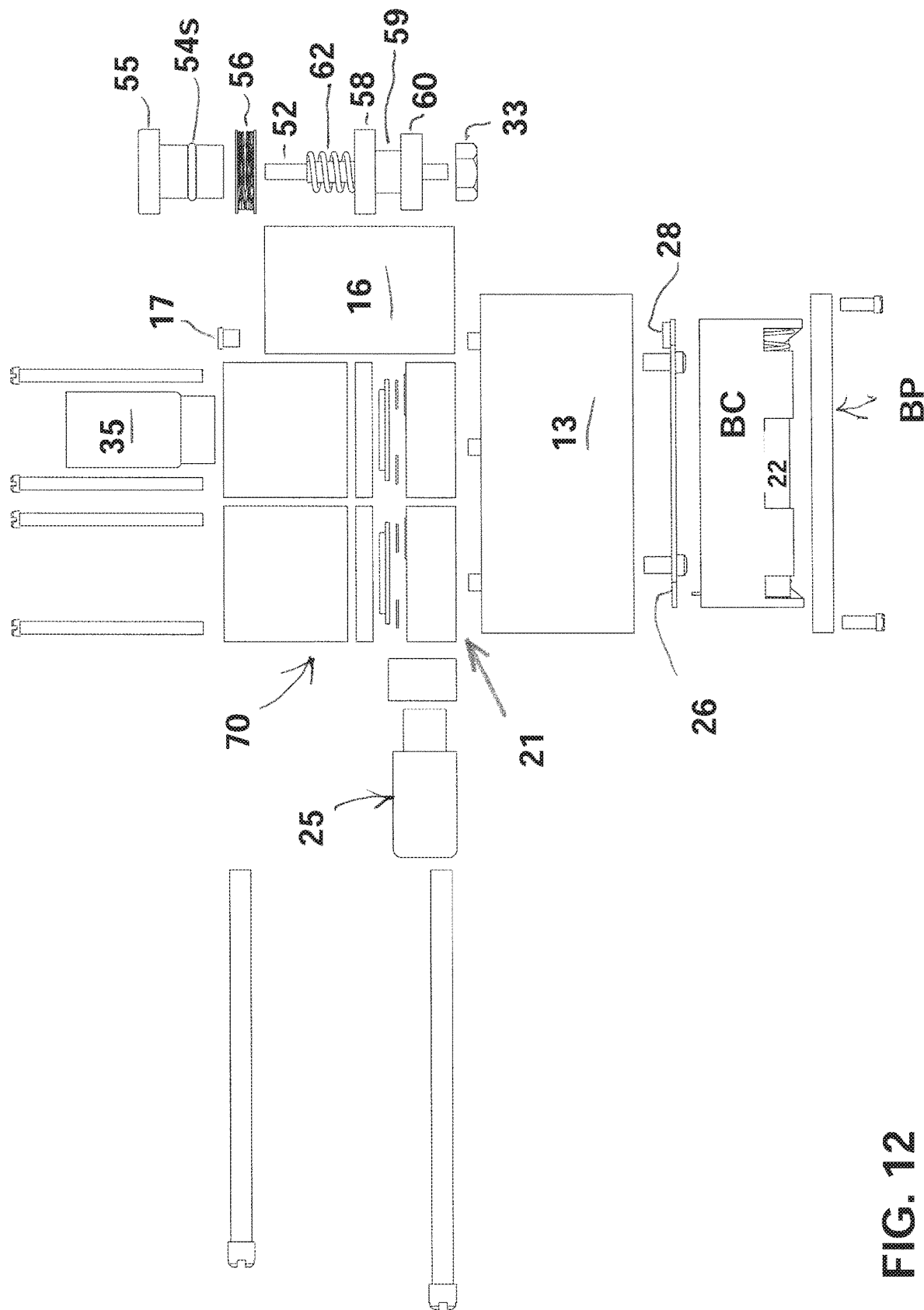
FIG. 12 is an exploded right side plan of the vaporizer apparatus according to the second embodiment.
Figure 13:
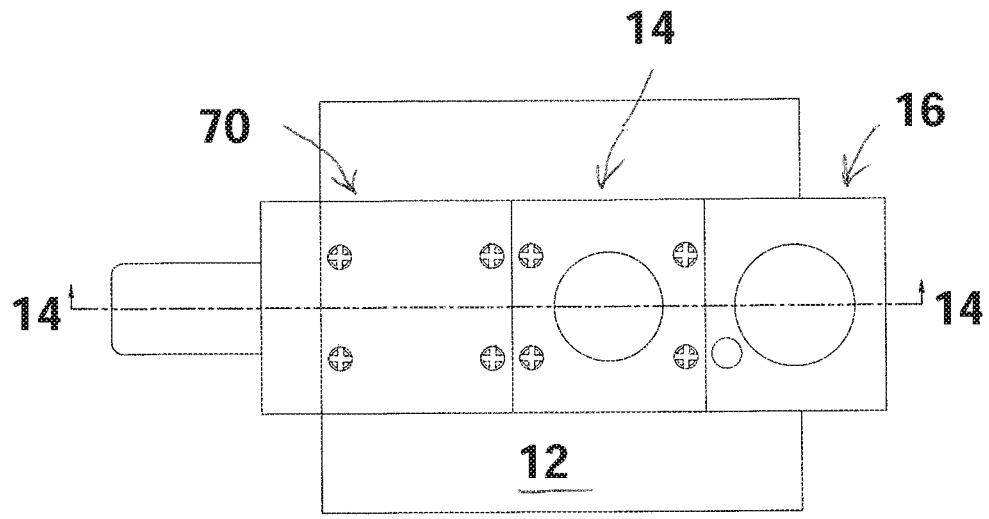
FIG. 13 is a top plan view of the vaporizer apparatus according to the second embodiment.
Figure 14:
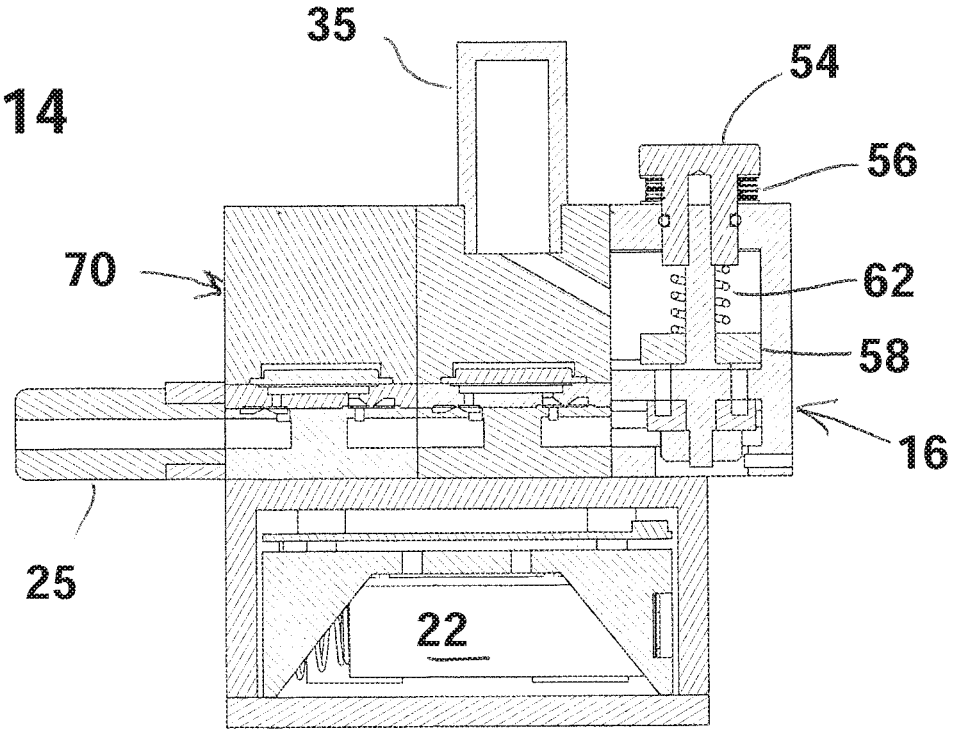
FIG. 14 is a cross section of the vaporizer apparatus according to the second embodiment, taken along the line 14-14 in FIG. 13.

A vaporizer apparatus 101 according to a second embodiment of the present invention is shown in FIGS. 10A-10B and 11-14. FIG. 10A is a perspective view of a vaporizer apparatus 101 as viewed from a right rear elevated vantage point according to the second embodiment of the present invention, and FIG. 10B is a perspective view of the vaporizer apparatus 101 of FIG. 10A as viewed from a lower right front vantage point. The vaporizer apparatus 101 of the second embodiment is similar to the vaporizer apparatus 10 according to the first embodiment as previously described, and shares many of the same modular components. Components of the vaporizer apparatus 101 according to the second embodiment, which are shared with the vaporizer apparatus 10 of the first embodiment, are given the same numbers in the drawings.

The primary difference between these two embodiments is that in the second embodiment, an additional pump 21 (FIG. 12) is provided housed in a second pump housing 70, which is similar to the first pump housing 14 except that it does not include any opening to receive a cartridge, and also does not include any oil inlet passage comparable to the oil inlet passage 15 of the first pump housing 14. The pump 21 of the second pump housing 70 is substantially identical to the pump 20 of the first pump housing 14.

The two pumps 20, 21 are connected in series. The reason for using the dual pumps 20, 21 in this second embodiment is to generate a quicker and more effective pressure reduction inside of the vacuum sealed chamber VSC of the chamber housing 16 than is possible using the single pump 20. Additional pumps may be included, if desired such that there are more than two pumps.

Operation of the vaporizer apparatus according to the second embodiment is similar to that according to the vaporizer of the first embodiment, except that the controller operates both of the pumps to quickly reduce the pressure in the oil chamber and evaporate the oil.

Third Embodiment

A vaporizer apparatus 110 according to a third embodiment of the present invention is shown in FIGS. 15-21. FIG.

15 is a perspective view of the vaporizer apparatus 110, according to the third embodiment of the present invention, as viewed from a right front elevated vantage point.

Figure 15:
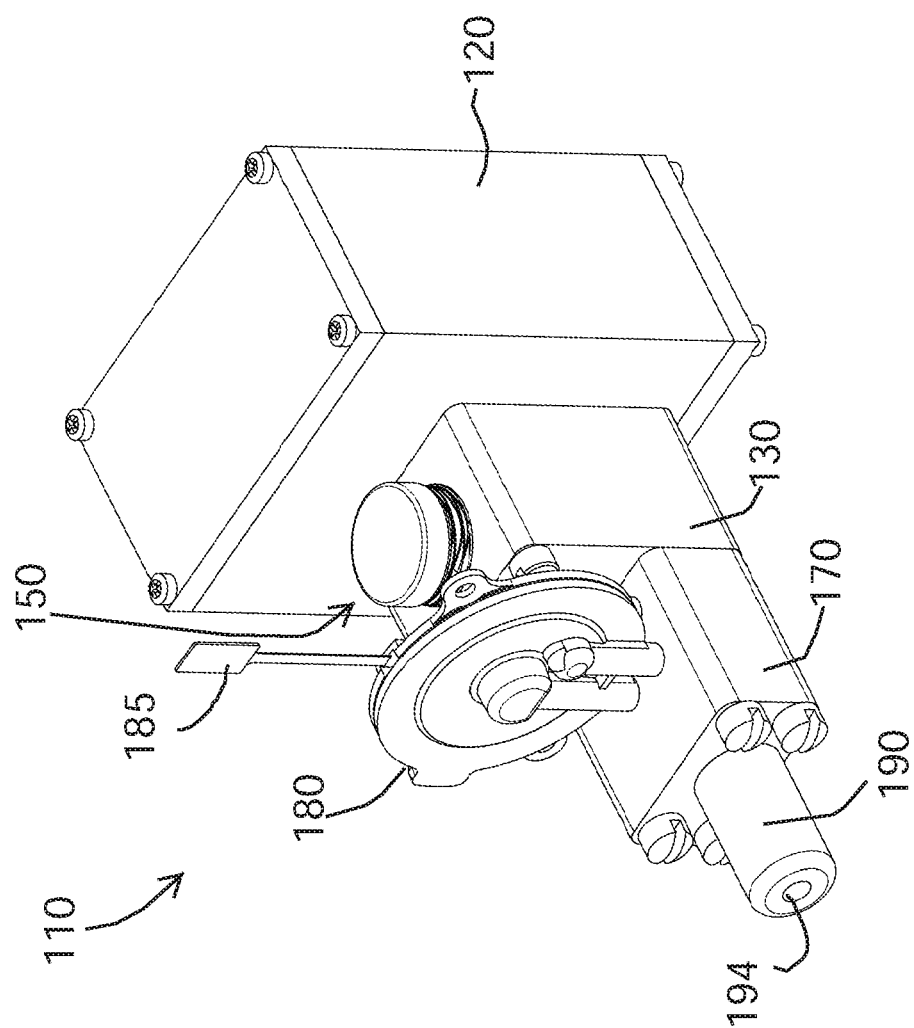
FIG. 15 is a perspective view of a vaporizer apparatus according to a third embodiment of the present invention, as viewed from a right front elevated vantage point.

As shown in FIG. 15, the vaporizer apparatus 110 generally includes a control housing (also referred to as a battery/circuit board housing) 120, a main housing 130 connected to the control housing 120, an operation unit 150 mounted into the main housing 130, a manifold 170 (also referred to as an air flow chamber) connected to the main housing 130, a pump 180 connected to the manifold 170, and a mouthpiece 190 connected to the manifold 170.

The pump 180 used in the present invention may be a piezo electric pump, a micro piezo electric pump, a piezo-electric diaphragm micropump, or any other type of pump which will work in the vaporizer apparatus 110.

The pump 180 may, optionally, be provided with an external power connector 185, which may be connected to a corresponding connector on the control housing 120. The manifold 170 and the pump 180 may be combined into a single housing to reduce part count, or may be integrally formed as one unit. The pump 180 may be disposed outside of the manifold 170, as shown, or alternatively, may be entirely concealed within the manifold 170, as it is in the first embodiment hereof.

It may be noted that, in the embodiment shown in FIG. 15, the control housing 120, the main housing 130, the manifold 170 and the mouthpiece 190 of the vaporizer apparatus 110 are arranged in series and are connected in this order.

Figure 16:
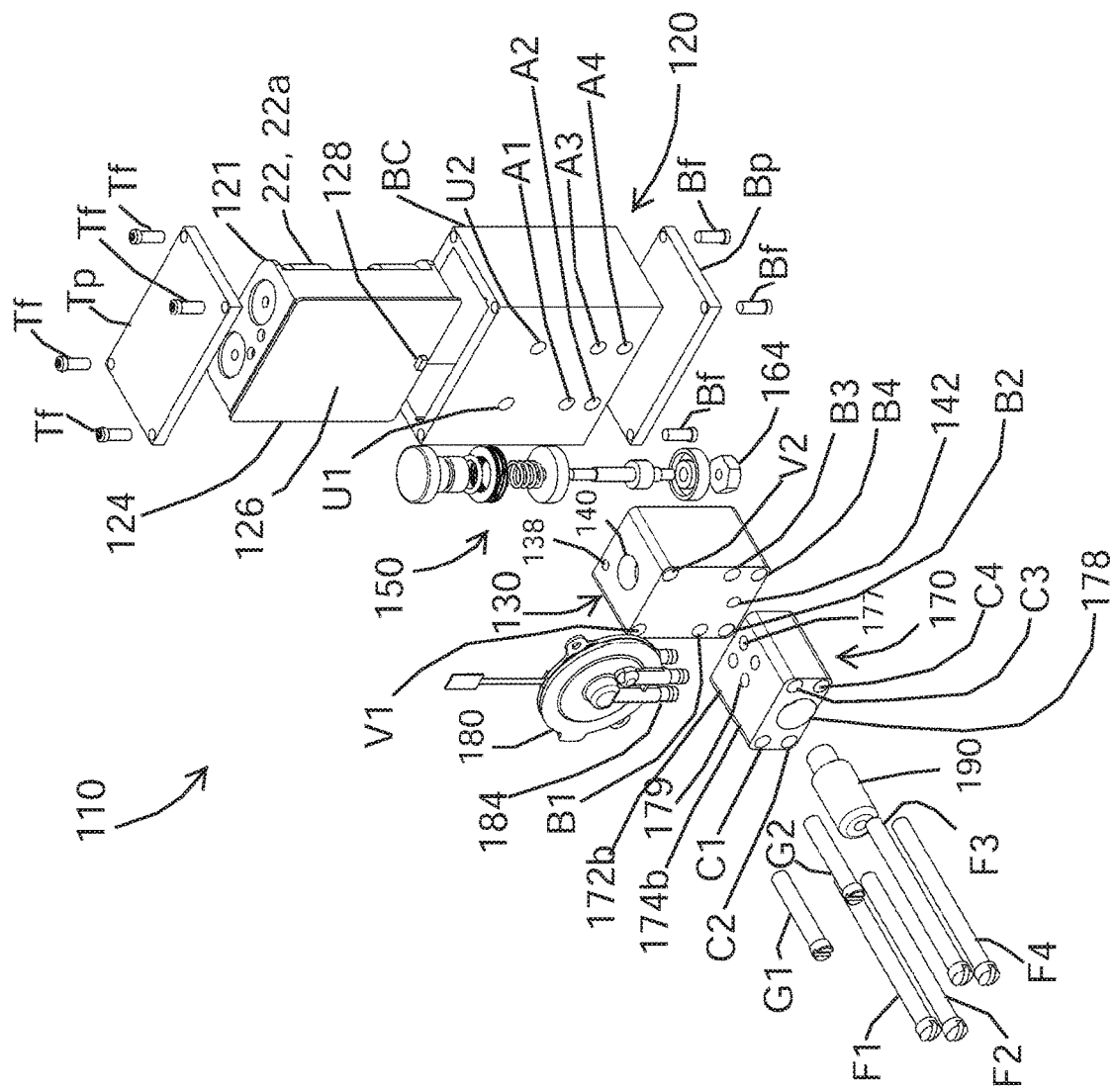
FIG. 16 is an exploded perspective view of the vaporizer apparatus of FIG. 15 as viewed from a right front elevated vantage point.
Figure 17:
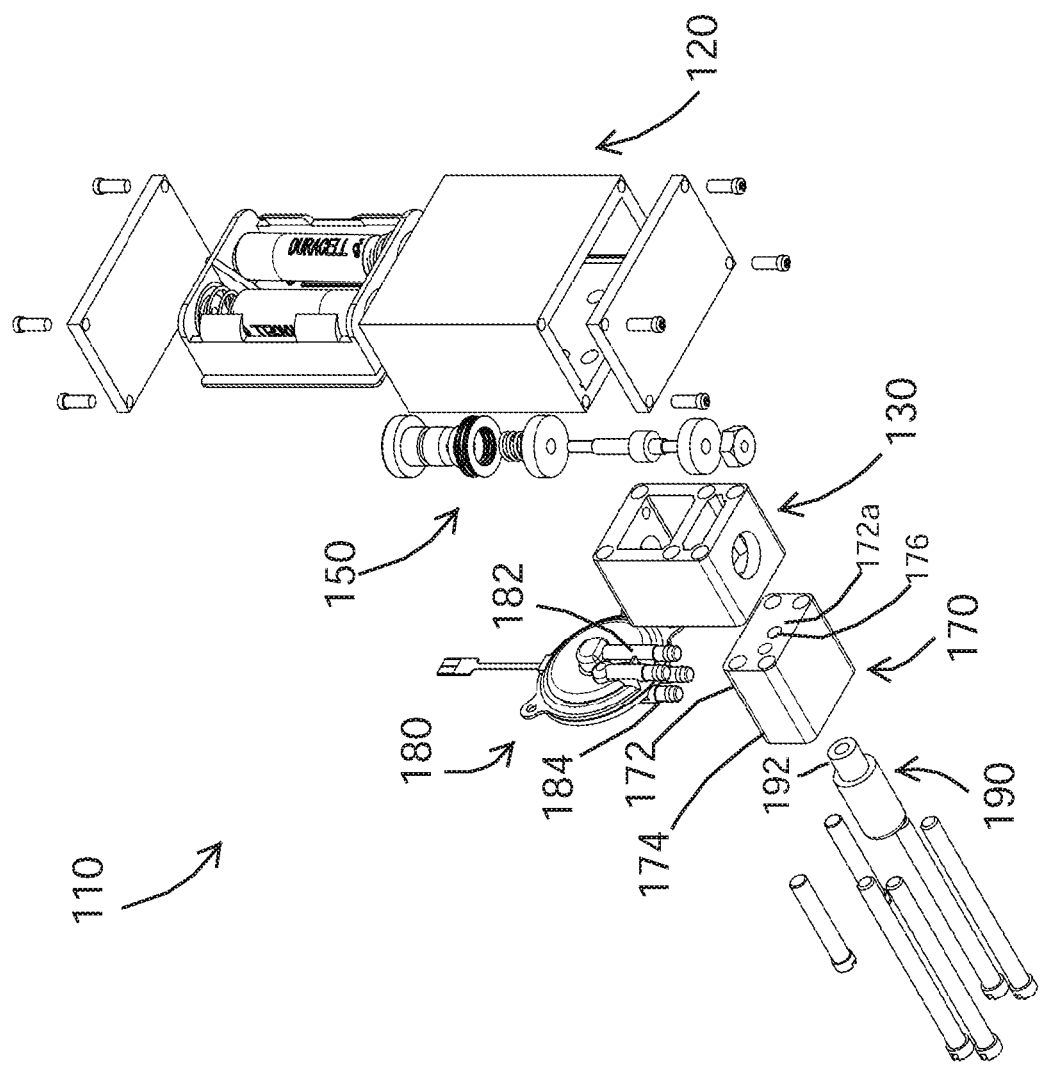
FIG. 17 is an exploded perspective view of the vaporizer apparatus of FIG. 15 as viewed from a right rear vantage point below the apparatus.

As it can be seen from FIG. 16, the vaporizer apparatus 110 of the third embodiment hereof has a modular structure. In other words, the vaporizer apparatus 110 includes several units, i.e., the control housing 120, the main housing 130, the operation unit 150, the manifold 170, and the mouthpiece 190, which are formed as individual units. However, in an alternative arrangement, the control housing 120, the main housing 130, manifold 170, and the mouthpiece 190 may be integrally formed as one unit structure.

FIG. 16 shows an exploded view of the vaporizer apparatus as viewed from an elevated right front vantage point. The control housing 120 may be a box-shaped housing as shown in FIGS. 15-19. Alternatively, if desired, the control housing 120 may be a cylindrically-shaped housing, a hexagonally-shaped housing or other suitably-shaped housing.

Figure 18:
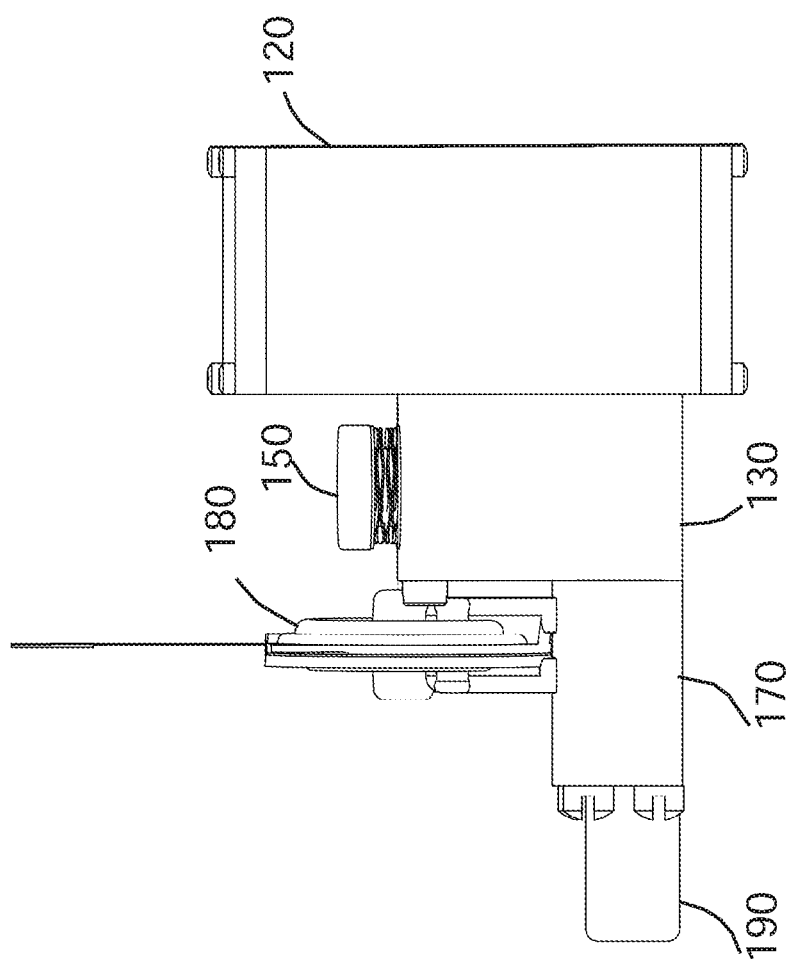
FIG. 18 is a right side plan view of the vaporizer apparatus according to the third embodiment.
Figure 19:
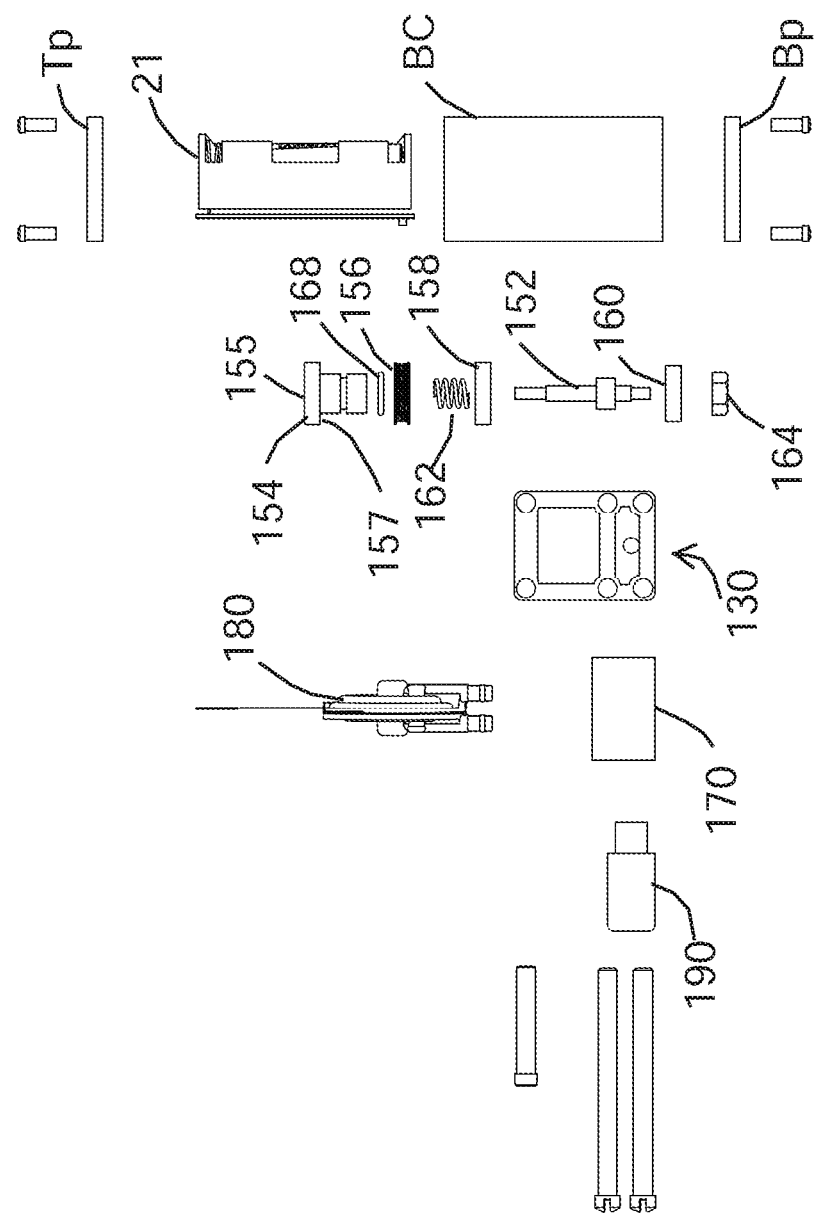
FIG. 19 is an exploded right side plan view of the vaporizer apparatus according to the third embodiment.
Figure 20:
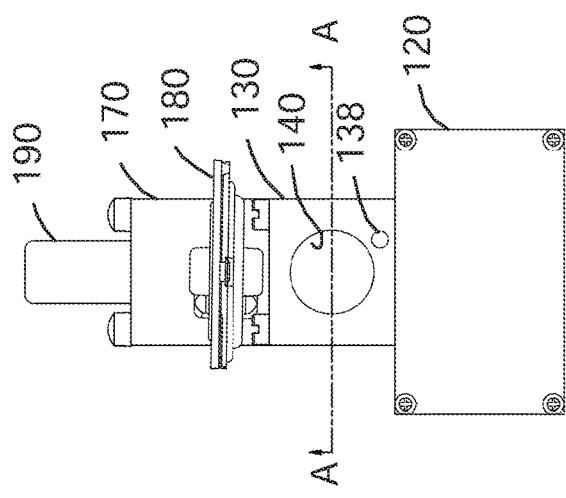
FIG. 20 is a top plan view of the vaporizer apparatus of FIG. 15.

As shown in FIG. 16, the control housing 120 has connecting holes A1, A2, A3, A4 formed therein. The main housing 130 has connecting holes B1, B2, B4 and B4 formed therein, which correspond with the respective connecting holes A1, A2, A3 and A4 of the control housing 120. Further, the manifold 170 has connecting holes C1, C2, C3 and C4, which correspond with the respective connecting holes A1, A2, A3 and A4 of the control housing 120, and also with the respective connecting holes B1, B2, B3 and B4 of the main housing 130. The control housing 120, the main housing 130 and the manifold 170 are connected with each other by using a plurality of fasteners F1, F2, F3 and F4 so as to arrange the control housing 120, the main housing 130 and the manifold 170 in series as shown in FIGS. 15, 18, and 20.

For example, the respective connecting holes A1, B1 and C1 of the control housing 120, the main housing 130 and the manifold 170 are aligned, and the control housing 120, the main housing 130 and the manifold 170 are connected with each other by fastening the fastener F1.

However, as discussed above, in another embodiment the control housing 120, the main housing 130 and the manifold 170 may be formed as one integrated unit.

Further, the control housing 120 has second connecting holes U1, U2 which correspond to second connecting holes V1, V2 of the main housing 130. The control housing 120 and the main housing 130 are additionally connected with each other by fastening the control housing 120 and the main housing 130 via the second connecting holes U1, U2 of the control housing 120 with the corresponding second connecting holes V1, V2 of the main housing 30 using second fasteners G1, G2, respectively.

The control housing 120 includes a battery chamber BC, and is configured to receive a battery holder 121, a control unit 124 and a position-sensing device 128 (which may be a Hall effect sensor, an activation switch or other position-sensing device). The battery holder 121 is configured to receive a battery 22 including one or more battery cells 22$a$ of suitable specification. The battery cells 22$a$ may be connected in series or parallel, and the plurality of battery cells 22$a$ are used to achieve a desired power.

The control unit 124 is mounted on the battery holder 121. The battery 22 is connected with each of the control unit 124 and the pump 180, and provides power thereto at a desired specification, e.g., at 3V. However, the control unit 124 and the pump 180 may receive a power from a different power source in addition to the battery 22 or separate from the battery 22.

In the embodiment depicted in FIG. 16, the control housing 120 further includes a top cover plate Tp and a bottom cover plate Bp. The top and bottom cover plates Tp, Bp are placed on top and bottom portions of the battery chamber BC, respectively. The top cover plate Tp is held in place on the top portion of battery chamber BC by using a plurality of top fasteners Tf, and the bottom cover plate Bp is held in place on the bottom portion of the battery chamber BC by using a plurality of bottom fasteners Bf.

The control unit 124 includes a circuit board 126. The position sensor 128 is connected to the circuit board 126, and provides input signal to the circuit board 126 when the operation unit 150 is operated (discussed below) and a position of the magnetic nut 164 is changed due to pressing of the knob 154. The position sensor 128 measures the magnitude of a magnetic field of the magnetic nut 164. The position sensor 128 and magnetic nut 164 are used to activate the control unit 124, but may be substituted with an activation switch or other mechanism.

The control unit 124 operates the pump 180 based on input received either from the position sensor 128, or from an activation switch or other mechanism. The control unit 124 may be placed on a back side of the battery holder 121. Optionally, the control unit 124 may also provide a charging circuit for the batteries 22$a$, as well as the modulation circuitry for the pump 180.

The main housing 130 is a box-shaped unit. The main housing 130 is disposed between the control housing 120 and the manifold 170.

Figure 21:
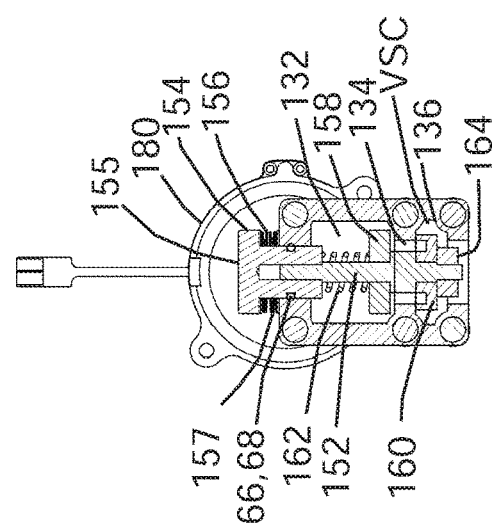
FIG. 21 is a sectional view of the vaporizer apparatus of FIG. 15, taken along the line A-A in FIG. 10, showing a vertical section through a main housing thereof.

As it can be seen from FIG. 21, the main housing 130 has an oil chamber 132, an oil reservoir 134 and an evacuation chamber 136 formed therein. The oil reservoir 134 is formed between the oil chamber 132 and the evacuation chamber 136. In other words, the oil reservoir is disposed along an oil path between the oil chamber 132 and the evacuation chamber 136.

Further, the main housing 130 has an oil-feeding hole 138 and an operation unit opening 140 formed therein. The oil-feeding hole 138 facilitates filling of oil in the oil chamber 132. A cap, similar to the cap 17 shown in FIG. 7, is provided for selectively opening and closing the oil-feeding hole 138. The operation unit opening 140 is configured to receive the operation unit 150 therein for arranging the operation unit 150 into the main housing 130.

Furthermore, the main housing 130 has an outlet opening 142 (FIG. 16) formed therein. The outlet opening 142 is connected with the manifold 170, specifically with an inlet opening 176 (FIG. 17) of the manifold 170.

The operation unit 150 is disposed in the operation unit opening 140 formed in the main housing 130. The operation unit 150 is operable to seal a top of the oil reservoir 134, and also to seal a bottom of the evacuation chamber 136, thereby trapping oil in the oil reservoir 134 and the evacuation chamber 136 and further creating a vacuum sealed chamber VSC.

The operation unit 150 includes a shaft 152, an operating knob (also referred to as a top button or a knob or an activation mechanism) 154 mounted on the shaft 152, and a stacked disc spring (top spring) 156 disposed between the top portion 114 of the main housing 130 and the operating knob 154. The operation unit 150 also includes a shaft spring 162 arranged on the shaft 152, specifically on a portion thereof disposed in the oil chamber 132 between a top seal 158 arranged at a top portion of the oil reservoir 134, and a bottom seal 160 disposed at a bottom portion of the evacuation chamber 136. The operation unit 150 further includes a magnetic nut 164, arranged below the bottom seal 160 on lower portion of the shaft 152.

The stacked disc spring 156, the shaft spring 162, the top seal 158, the bottom seal 160 and the magnetic nut 164 are concentrically and sequentially arranged along the shaft 152 from top to bottom, as shown.

A rubber O-ring seal 168 is disposed between the operation unit opening 140 of the main housing 130 and the operating knob 154. The operating knob 154 has an upper portion 155 and a lower portion 157. The top spring 156, which may be a stacked disk spring, is mounted between a lower portion 157 of the operating knob 154 and an outer (upper) portion of the main housing 130.

The manifold (also referred to as an air flow chamber) 170 is a box-shaped unit. However, the manifold may be of a cylindrical shape. Optionally, the manifold 170 may be omitted, may be modified in shape, or may be combined with the main housing 130 as an integral unit.

Where used, the manifold 170 includes a first chamber 172, and a second chamber 174, which is separate from the first chamber 172. The first chamber 172 is disposed next to the main housing 130. A first side wall 172a of the first chamber 172 has an inlet opening 176 formed therein. The inlet opening 176 of the first chamber 172 is connected with the outlet opening 142 of the main housing 130. A first top wall 172b of the first chamber 172 has one or more first connector openings 177 formed therein. The first connector opening 177 is configured to receive an inlet 182 (also referred to as a suction end pipe) of the piezo pump 180.

In a modified embodiment, the manifold 170 and the pump 180 may be combined into a single housing to reduce cost and part count. In other words, one or more pumps 180 may be disposed inside of the manifold 170 such that manifold 170 and the pump 180 cooperate to form one single unit.

The second chamber 174 includes a second side wall 174a having an outlet opening 178 formed therein. The outlet opening 178 is configured to receive an inlet opening 192 (FIG. 17) of the mouthpiece 190. Further, the second chamber 174 includes a second top wall 174b having one or more second connector openings 179 formed therein. The second connector opening 177 is configured to receive an outlet 184 (also referred to as a discharge end pipe) of the piezo pump 180.

The pump 180 is a disc pump, which is a high-performance piezoelectric micropump operating through ultrasonic acoustic resonance. The disc pump can be applied to the pressure-driven flow of liquids. The pump 180 has compact form factor, i.e., it has high portability and it can be tightly integrated into portable devices such as the vaporizer apparatus of the present invention. An operational cross section showing a sequence of operation of a piezo pump is shown in FIGS. 8A-8B.

The mouthpiece 190 is a cylindrical unit. The mouthpiece has an inlet opening 192 (FIG. 17) formed at one end thereof, and an outlet opening 194 (FIG. 15) formed at the other end thereof. The inlet opening 192 is connected to the outlet opening 178 of the second chamber 174 of the manifold 170.

According to the present invention, upon operation of the operation unit 150, the top seal 158 isolates the oil reservoir 134 from the oil chamber 132, and the bottom seal 160 seals the bottom of the evacuation chamber 136, whereupon a vacuum seal is created which causes lowering of pressure for the oil trapped in the oil reservoir 134 and evacuation chamber 136. Further, when the piezo pump 180 is automatically triggered upon formation of the vacuum seal, i.e. turned on, the pressure is reduced to a value that causes oil that is trapped in the oil reservoir 134 and evacuation chamber 136 to vaporize, and the resulting vapor to flow from the outlet opening 142 to the first chamber 172, then to the second chamber 174 of the manifold 170, and further to the mouthpiece 190.

In other words, when the operation unit 150 is operated, i.e., by pressing down the knob (top button) 154 thereof, the shaft 152 is pushed down along with the knob 154, until the top seal 158 (top rubber block) seals of the top of the oil reservoir 134 while trapping oil in the oil reservoir 134. The shaft spring 162 is then further compressed until the bottom seal (bottom rubber block) 160 seals the bottom of the evacuation chamber 136, thereby creating a vacuum sealed chamber.

Once the vacuum seal is created, the magnetic nut 164 will have reached a point to trigger the position sensor 128, which is operatively connected to the circuit board 126 of the control unit 124 that turns the pump 180 on when the position sensor 128 is triggered. The pump 180 is powered by the battery 22. Upon the turning the pump 180 on, the pressure is greatly reduced, causing the oil that was trapped in the oil reservoir 34 and evacuation chamber 36 to vaporize and flow though the manifold (also referred to as an air flow chamber), out through the mouthpiece.

The oil that was trapped in the oil reservoir 134 and evacuation chamber 136 is not heated or subjected to any heat source for vaporization thereof. Rather, the oil that was trapped in the oil reservoir 134 and evacuation chamber 136 is subjected to a very low pressure, for example, at 1007 mbar or below, for vaporization thereof. Specifically, when the operation unit 150 is operated, the oil reservoir 134 and the evacuation chamber 136 are isolated from the oil chamber 132, thereby creating the vacuum sealed chamber VSC.

Displacement of the shaft 152 also causes further displacement of the magnetic nut 164 that reaches a point of triggering the position sensor 128 that provides signal to the control unit 24 to switch on the pump 180, which further reduces the pressure differential, for example, at or below 1007 mbar, in the vacuum sealed chamber VSC causing vaporization of the oil at or below a room temperature without subjecting the oil to a heat source such as, e.g., a heating element. The vapor is moved to the second chamber 174 of the manifold 170 and then to the mouthpiece 190. The vapor in the mouthpiece 190 can be inhaled by the user through the outlet opening 194 of the mouthpiece 190.

In a modified embodiment, the mouthpiece may act as an activation mechanism for the operation unit. For example, when a user inhales through the mouthpiece, it may trigger the operation unit without the user pressing a knob to turn on the operation unit.

Since the oil is vaporized with no heat source and at or below an ambient room temperature, vapor thus produced is at a low temperature that is not hot. Thus, the vaporizer apparatus 110 of the present invention cannot cause any heat related injury to a user. Moreover, since the oil is not heated or is not subjected to a heat source of any kind, the alteration of composition of the oil due to heat can be reduced or prevented.

Fourth Embodiment

Figure 22:
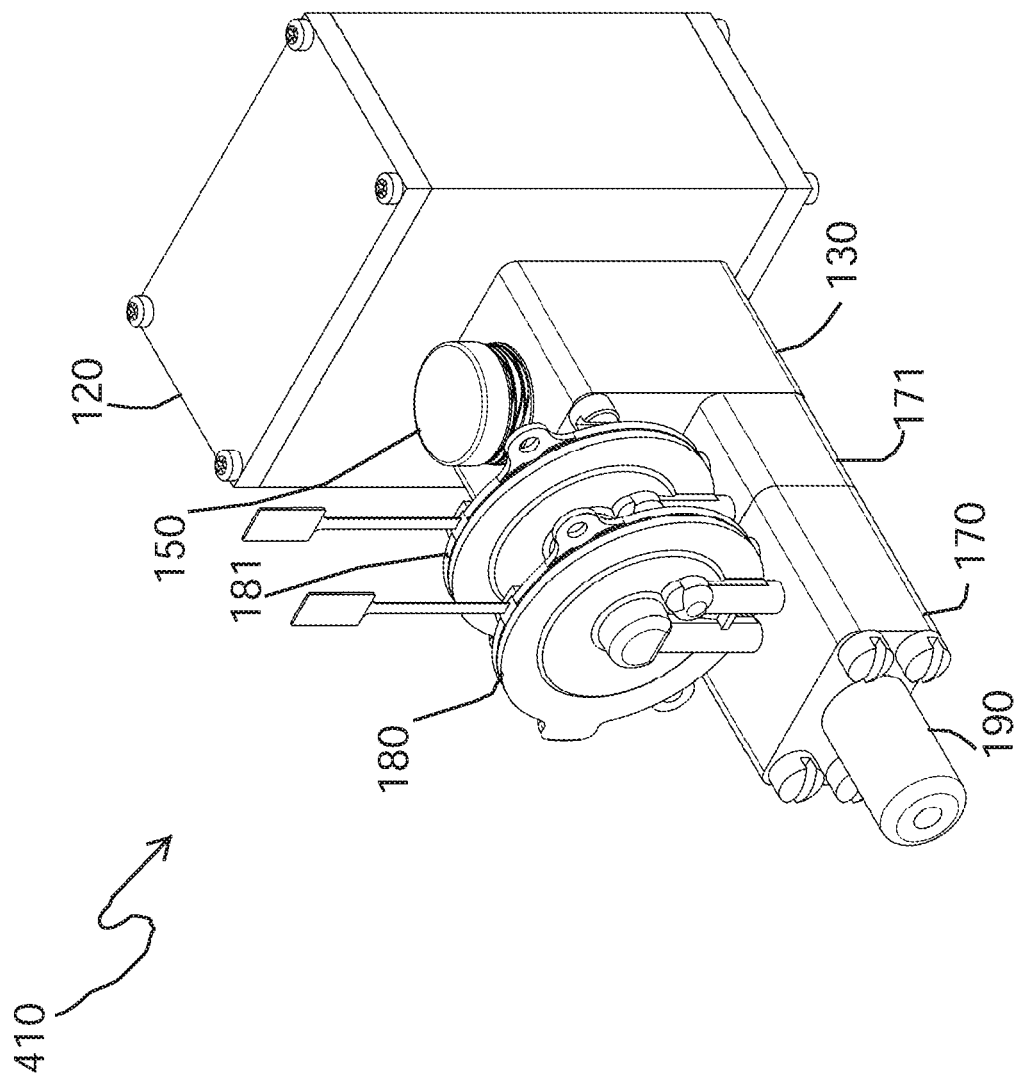
FIG. 22 is a perspective view of a vaporizer apparatus according to a fourth embodiment hereof, as viewed from right front top.

A vaporizer apparatus 410 according a fourth embodiment of the present invention is shown in FIGS. 22-27. FIG. 22 is a perspective view of a vaporizer apparatus according to the fourth embodiment, as viewed from an elevated right front vantage point.

Figure 23:
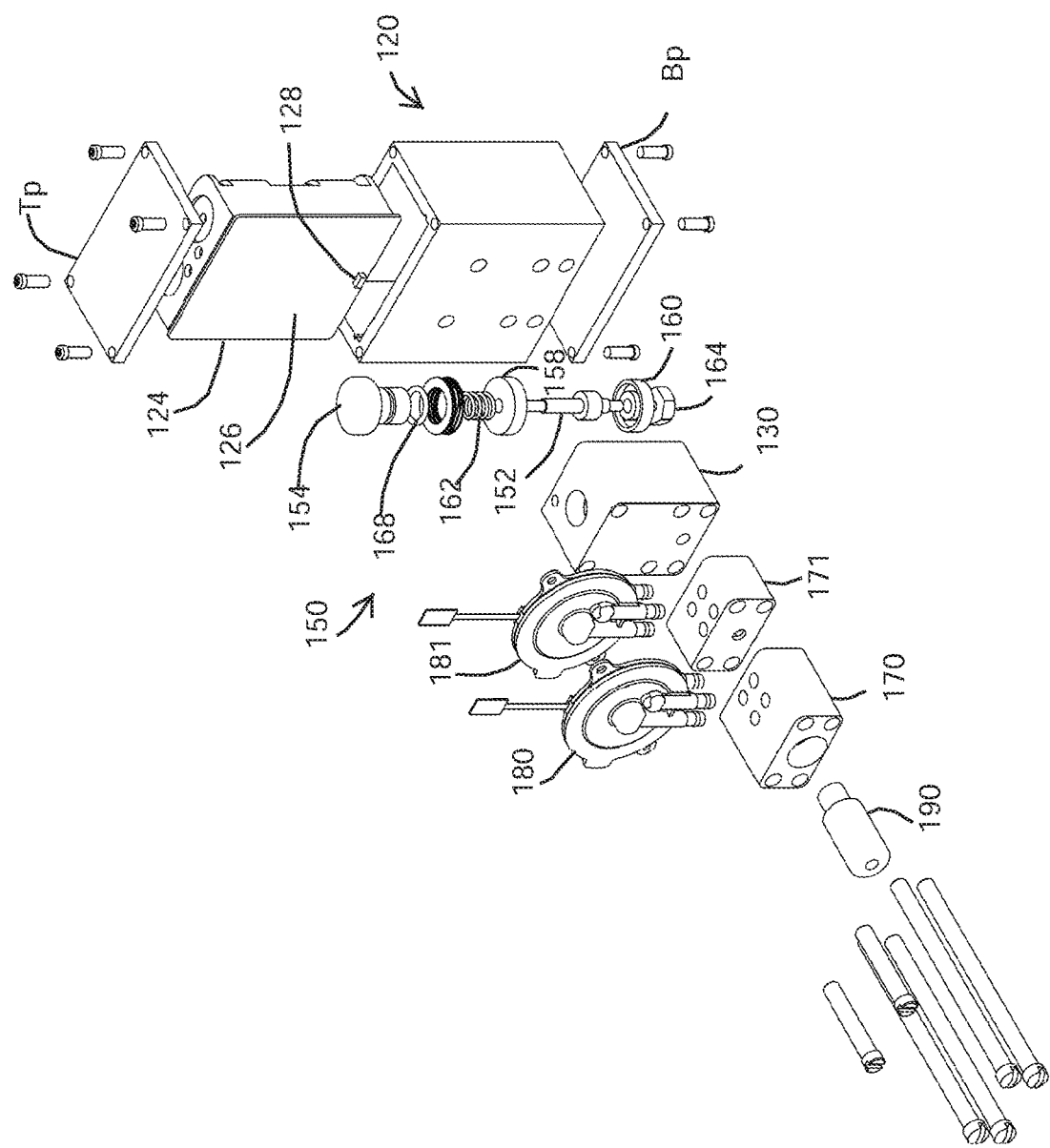
FIG. 23 is an exploded view of the vaporizer apparatus of FIG. 22, as viewed from right front top.
Figure 24:
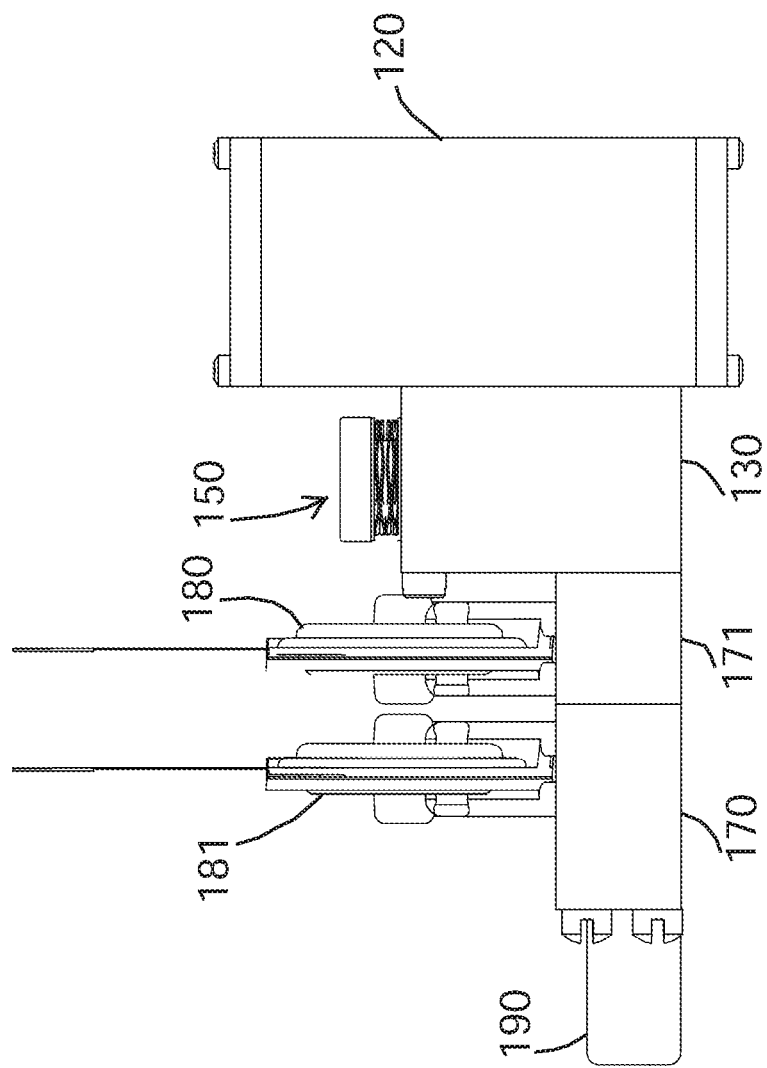
FIGS. 24 and 25 show a right side view and exploded right side view, respectively, of the vaporizer apparatus according to the fourth embodiment.
Figure 25:
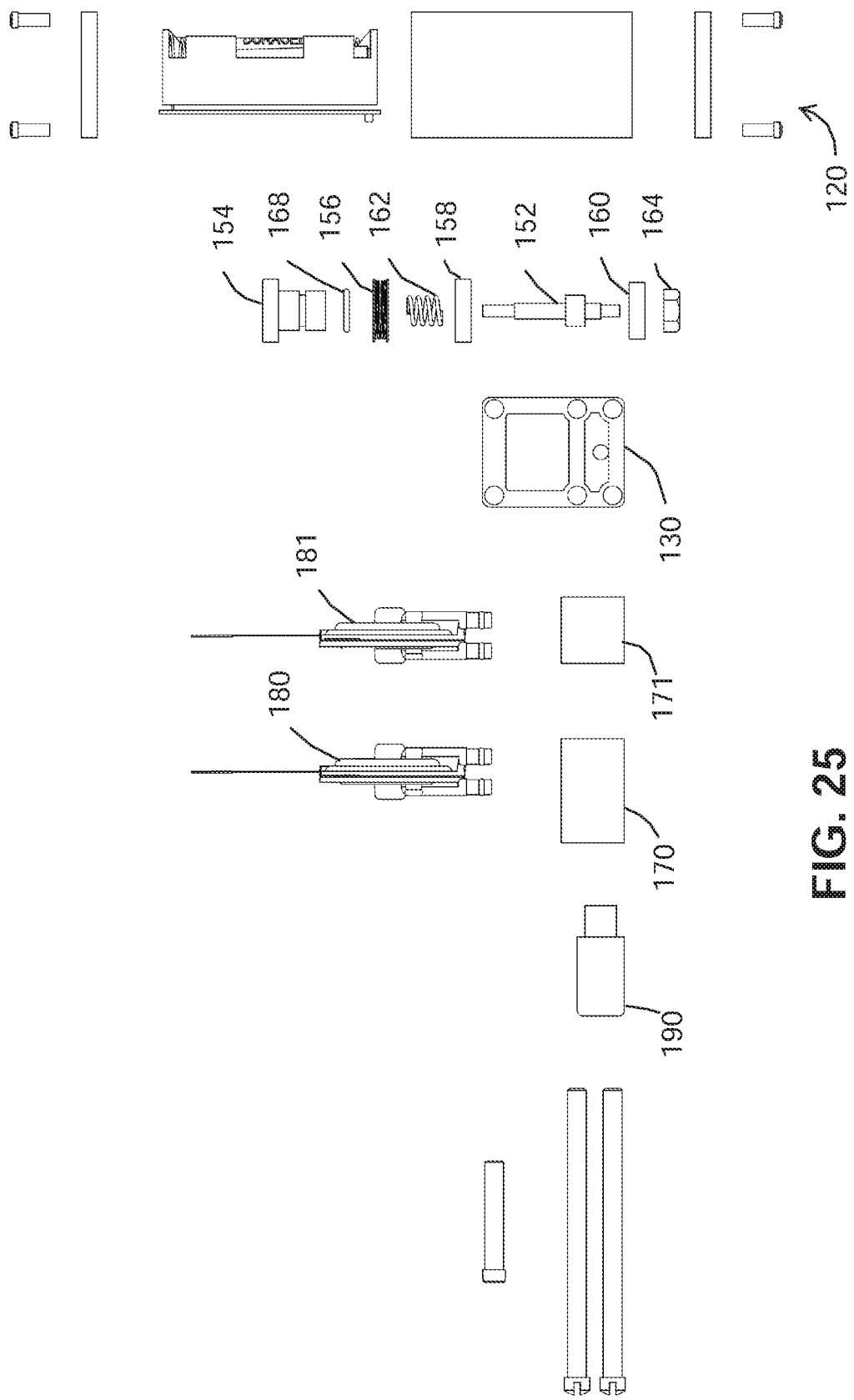

FIG. 23 is an exploded view as viewed from an elevated right front vantage point. FIGS. 24 and 25 show a right side view and an exploded right side view, respectively. FIG. 26 is a top plan view, and FIG. 27 is a sectional view, taken along the line 27-27 in FIG. 26, of the vaporizer apparatus according to the fourth embodiment of the present invention.

It can be seen from FIGS. 22-27, that the vaporizer apparatus 410 according to the fourth embodiment of the present invention is different from the third embodiment in that the fourth embodiment includes two pumps—a first pump 180 (which is similar to the pump 180 of the third embodiment) and a second pump 181, and two manifolds—a first manifold 170 (which is similar to the manifold 170 of first embodiment) and a second manifold 171, on which the second pump 181 is mounted.

The second manifold 171 is arranged between the first manifold 170 and the main housing 130. Additional pumps and manifolds may be included, such that there are two or more piezoelectric pumps and two or more manifolds.

Alternatively, a plurality of pumps may be mounted in or on one manifold. The second manifold 171 has an inlet portion connected with main housing, specifically oil outlet thereof, and an outlet portion, which is connected with the inlet portion of the manifold such that the two pumps 180 and 181 are arranged in series. However, pumps 180, 181, which may be more than two, may be arranged in different combination. Further, the pumps may have similar or different specifications.

The vaporizer apparatus 410 of the fourth embodiment is operated in a similar manner as the vaporizer apparatus 110 of the third embodiment, with the exception that both the pumps 180 and 181 are activated when the operation unit 150 is operated.

Method of Use

The present invention also relates to a method of evaporating a liquid in a vaporizing apparatus to generate a vapor.

The method includes a first step of sealing a chamber with a quantity of liquid therein by closing a valve.

The method includes another step of activating a vacuum pump which communicates with the chamber via an activation passage, and operating the pump to reduce a pressure inside of the chamber until the liquid evaporates.

The method includes another step of opening the valve after the liquid has evaporated to place the chamber into communication with an outlet.

The method includes a final step of drawing the vapor outwardly from the chamber via the outlet.

Optionally, in performing the method hereof, the vaporizing apparatus contains a control circuit, and when a user holds an activation button down, the control circuit sends 100% power to the pump and maintains the power at 100% as long as a user holds the activation button down.

When the user releases the activation button, a vacuum seal is released, and the power to the pump is reduced to a user-adjustable level and remains on for a user-adjustable time period.

Although the present invention has been described herein with respect to several specific illustrative embodiments, the foregoing description is intended to illustrate, rather than to limit the invention. Those skilled in the art of vaporizers will realize that many modifications of the illustrative embodiment can be made and would be operable. All such modifications, which are within the scope of the claims, are intended to be within the scope and spirit of the present invention.

What is claimed is:

1. A vaporizer apparatus comprising:
   a main housing having an evacuation chamber formed therein with an air inlet and an air outlet which communicates with the evacuation chamber;
   an operation unit operatively attached to the main housing and configured to be operated by a user, the operation unit configured to selectively and temporarily seal the evacuation chamber off from communication with the air inlet;
   at least one pump operatively connected to the main housing, the at least one pump being in fluid communication with the evacuation chamber, the at least one pump operable to selectively generate a low pressure environment in the evacuation chamber at an ambient temperature; and
   a mouthpiece attached to the main housing and configured to be selectively placed in fluid communication with the air outlet of the evacuation chamber;
   wherein the vaporizer apparatus is configured and arranged so that, when an oil is placed in the evacuation chamber and the operation unit is operated, the evacuation chamber is temporarily sealed off from the inlet, thereby creating a vacuum sealed chamber connected with the at least one pump, and the at least one pump is activated to reduce pressure in the evacuation chamber, whereby the oil is vaporized at an ambient temperature without requiring a heater,
   and when the operation unit is released, the evacuation chamber is placed into fluid communication with the air inlet and the mouthpiece.

2. The vaporizer apparatus according to claim 1, wherein said operation unit comprises a top seal arranged at a top portion of the evacuation chamber, and a bottom seal disposed in the evacuation chamber below the top seal.

3. The vaporizer apparatus according to claim 1, wherein said operation unit comprises a shaft and a magnetic nut mounted at one end portion of the shaft.

4. The vaporizer apparatus according to claim 3, further comprising a control unit comprising a microprocessor and a position sensor in communication with the control unit.

5. The vaporizer apparatus according to claim 1, wherein the main housing has an oil reservoir formed therein, and wherein said operation unit comprises:

a shaft,
a knob mounted on one end portion of the shaft;
a top seal arranged a top portion of the oil reservoir;
a shaft spring mounted on the shaft between the knob and the top seal;
a bottom seal disposed in the evacuation chamber and mounted on the shaft below the top seal;
and further wherein the apparatus is configured such that when said knob is pressed, the top seal moves inwardly and seals a top of the evacuation chamber, and the bottom seal seals a bottom of the evacuation chamber.

6. The vaporizer apparatus according to claim 1, wherein said pump is a piezoelectric micro pump.

7. The vaporizer apparatus according to claim 1, further comprising a replaceable cartridge containing a vaporizable liquid.

8. A vaporizer apparatus comprising:
a main housing having an evacuation chamber formed therein with an air inlet and an air outlet which communicates with the evacuation chamber;
an operation unit operatively attached to the main housing and configured to be operated by a user, the operation unit configured to selectively and temporarily seal the evacuation chamber off from communication with the air inlet;
a plurality of pumps operatively connected to the main housing, the pumps being in fluid communication with the evacuation chamber, the pumps operable to selectively generate a low pressure environment in the evacuation chamber at an ambient temperature; and
a mouthpiece attached to the main housing and configured to be selectively placed in fluid communication with the air outlet of the evacuation chamber;
wherein the vaporizer apparatus is configured and arranged so that, when an oil is placed in the evacuation chamber and the operation unit is operated, the evacuation chamber is temporarily sealed off from the inlet, thereby creating a vacuum sealed chamber connected with the pumps, and the pumps are activated to reduce pressure in the evacuation chamber, whereby the oil is vaporized at an ambient temperature without requiring a heater,
and when the operation unit is released, the evacuation chamber is placed into fluid communication with the air inlet and the mouthpiece.

9. The vaporizer apparatus according to claim 8, wherein said operation unit comprises a top seal arranged at a top portion of the evacuation chamber, and a bottom seal disposed in the evacuation chamber below the top seal.

10. The vaporizer apparatus according to claim 8, wherein said operation unit comprises a shaft and a magnetic nut mounted at one end portion of the shaft.

11. The vaporizer apparatus according to claim 10, further comprising a control unit comprising a microprocessor and a position sensor in communication with the control unit.

12. The vaporizer apparatus according to claim 8, wherein the main housing has an oil reservoir formed therein, and wherein said operation unit comprises:
a shaft,
a knob mounted on one end portion of the shaft;
a top seal arranged a top portion of the oil reservoir;
a shaft spring mounted on the shaft between the knob and the top seal;
a bottom seal disposed in the evacuation chamber and mounted on the shaft below the top seal;
and further wherein the apparatus is configured such that when said knob is pressed, the top seal moves downwardly and seals a top of the evacuation chamber, and the bottom seal seals a bottom of the evacuation chamber.

13. The vaporizer apparatus according to claim 8, wherein said pump is a piezoelectric micro pump.

14. The vaporizer apparatus according to claim 8, further comprising a replaceable cartridge containing a vaporizable liquid.

15. A method of evaporating a liquid in a vaporizing apparatus to generate a vapor, said method comprising the steps of:
a) sealing a chamber with a quantity of liquid therein by closing a valve;
b) activating at least one vacuum pump which communicates with the chamber via an activation passage, and operating the pump without heating the liquid to reduce a pressure while substantially maintaining an ambient temperature inside of the chamber until the liquid evaporates to form the vapor;
c) opening the valve to place the chamber into communication with an outlet; and
d) drawing the vapor outwardly from the chamber via the outlet,
wherein the apparatus is configured to provide the vapor to a user for inhalation thereof, and includes a mouthpiece in communication with the outlet.

16. The method of claim 15, wherein the vaporizing apparatus contains a control circuit, and when a user holds an activation button down, the control circuit sends 100% power to the at least one pump and maintains the power at 100% as long as a user holds the activation button down;
and when the user releases the activation button, a vacuum seal is released, and the power to the at least one pump is reduced to a user-adjustable level and remains on for a user-adjustable time period.

* * * * *